US007684031B2

(12) United States Patent
Yokota et al.

(10) Patent No.: US 7,684,031 B2
(45) Date of Patent: Mar. 23, 2010

(54) VISUAL INSPECTION APPARATUS, VISUAL INSPECTION METHOD, AND PERIPHERAL EDGE INSPECTION UNIT THAT CAN BE MOUNTED ON VISUAL INSPECTION APPARATUS

(75) Inventors: Atsutoshi Yokota, Kamiina-gun (JP); Hiroyasu Hebiishi, Tokyo (JP); Shinichi Dosaka, Tsukui-gun (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/977,880

(22) Filed: Oct. 26, 2007

(65) Prior Publication Data
US 2008/0088833 A1 Apr. 17, 2008

(51) Int. Cl.
*G01N 21/00* (2006.01)
(52) U.S. Cl. .................... 356/237.1; 356/237.2
(58) Field of Classification Search ... 356/237.1–237.5; 73/865.8–865.9; 414/226.01–226.05; 382/145; 250/548
See application file for complete search history.

(56) References Cited

U.S. PATENT DOCUMENTS

| | | | | |
|---|---|---|---|---|
| 4,065,212 A | * | 12/1977 | Belleson et al. | 356/398 |
| 6,034,766 A | * | 3/2000 | Sugiura et al. | 356/239.1 |
| 2002/0134179 A1 | | 9/2002 | Maruyama et al. | |
| 2003/0169916 A1 | * | 9/2003 | Hayashi et al. | 382/145 |
| 2003/0202178 A1 | | 10/2003 | Tsuji et al. | |
| 2003/0222229 A1 | | 12/2003 | Taniguchi et al. | |

FOREIGN PATENT DOCUMENTS

| JP | 5-160245 A | 6/1993 |
|---|---|---|
| JP | 8-136462 A | 5/1996 |
| JP | 09-269298 A | 10/1997 |
| JP | 2002-270672 A | 9/2002 |
| JP | 2002-313863 A | 10/2002 |
| JP | 2003-243465 A | 8/2003 |
| JP | 2003-344307 A | 12/2003 |
| JP | 2004-096078 A | 3/2004 |
| JP | 2004-96078 A | 3/2004 |
| WO | WO 02/21589 A1 | 3/2002 |
| WO | WO 03/028089 A1 | 4/2003 |

* cited by examiner

*Primary Examiner*—Gregory J Toatley, Jr.
*Assistant Examiner*—Tri T Ton
(74) *Attorney, Agent, or Firm*—Frishauf, Holtz, Goodman & Chick, P.C.

(57) ABSTRACT

This visual inspection apparatus has a macro-inspection section and a micro-inspection section. In the micro-inspection section, a inspection stage and a microscope are loaded into a loading plate. The inspection stage can be moved in any directions of the X, Y, and Z directions, and can also be rotated in the θ direction. Moreover, a peripheral edge inspection section that acquires an enlarged image of a peripheral edge of wafer W is fixed to the loading plate. The peripheral edge inspection section is arranged so as to image the peripheral edge of wafer W held by the inspection stage.

8 Claims, 13 Drawing Sheets

(STATE AT THE TIME OF OBSERVATION OF UPPER SURFACE OF WAFER)

(STATE AT THE TIME OF OBSERVATION OF SIDE SURFACE OF WAFER)

(STATE AT THE TIME OF OBSERVATION OF LOWER SURFACE OF WAFER)

(MONITOR IMAGE) AT THE TIME OF LOW MAGNIFICATION OBSERVATION

Figure 1:
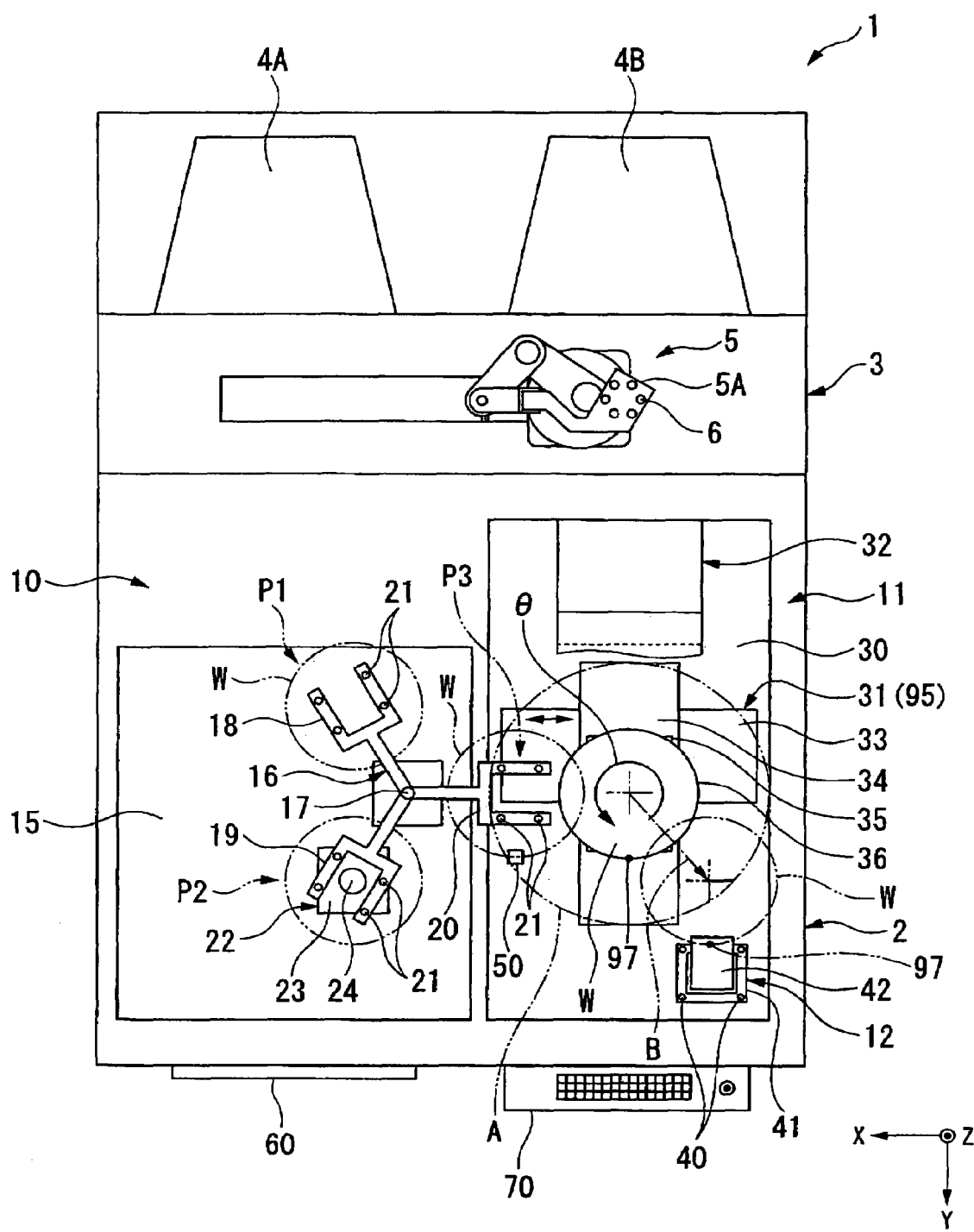

VISUAL INSPECTION APPARATUS, VISUAL INSPECTION METHOD, AND PERIPHERAL EDGE INSPECTION UNIT THAT CAN BE MOUNTED ON VISUAL INSPECTION APPARATUS

BACKGROUND OF THE INVENTION

1. Field of the Invention

The present invention relates to a visual inspection apparatus used to inspect the appearance of a workpiece, a visual inspection method, and a peripheral edge inspection unit that can be mounted on such a visual inspection apparatus and used to inspect the peripheral edge of the workpiece.

2. Description of Related Art

When patterns, such as circuits, on a workpiece, such as a semiconductor wafer, are formed, a visual inspection apparatus that inspects the existence of a defect on the surface of the workpiece is used. As this type of visual inspection apparatus, there is an inspection apparatus (for example, refer to Patent Document 1) that oscillates and rotatably holds a workpiece, has a macro-inspection section that allows an inspector to visually inspect the surface of the workpiece (macro inspection), and a micro-inspection section that acquires an enlarged image of the workpiece to allow inspection (micro inspection), and that enables such macro inspection and micro inspection by use of one apparatus.

Further, when circuits, etc. are formed on a workpiece, warpage or internal stress may be caused in the workpiece due to heat treatment, etc. If such warpage and internal stress become large, the workpiece may be fractured during manufacture of the circuits. Thus, a technique of enlarging and observing the peripheral edge of the workpiece in advance, thereby inspecting the existence of cracks which may becomes fractures in the future, is known. As a visual inspection apparatus used to inspect the peripheral edge of the workpiece (peripheral edge inspection), there is an inspection apparatus (for example, refer to Patent Document 2) including a support that rotatably supports a workpiece, a peripheral edge imaging section that continuously captures images of the peripheral edge of the workpiece, and a peripheral edge illumination device that illuminates the peripheral edge.

[Patent Document 1] JP-A-2004-96078
[Patent Document 2] JP-A-2003-243465

However, in order to carry out the macro inspection, micro inspection, and peripheral edge inspection, there are problems in that a wafer must be replaced and moved by a machine, a loader, etc., between the visual inspection apparatus disclosed in Patent Document 1, and the visual inspection apparatuses disclosed in Patent Document 2, causing prolonged takt time. Further, when one visual inspection apparatus is attached to another visual inspection apparatus externally, transport time can be shortened. However, replacement of a workpiece is required even in such a case. Moreover, the installation area as the whole apparatus is not different from when apparatuses are installed independently.

SUMMARY OF THE INVENTION

The invention has been made in view of the above circumstances. It is therefore a main object of the invention is to reduce takt time, miniaturize the apparatus, and simplify the configuration of the apparatus in performing macro inspection, micro inspection, and peripheral edge inspection.

In order to solve the above problems, the invention provides a visual inspection apparatus including: a visual inspection section for performing visual inspection of the surface of a workpiece, and a peripheral edge inspection section that acquires an enlarged image of a peripheral edge of the workpiece. Here, a holding unit that holds the workpiece in the visual inspection section is shared by the visual inspection section and the peripheral edge inspection section.

Further, the invention provides a visual inspection method including: holding a workpiece by a holding unit and inspecting the appearance of the surface of the workpiece; bringing a peripheral edge inspection section that acquires an enlarged image of a peripheral edge of the workpiece relatively close to the holding unit; and acquiring the enlarged image of the peripheral edge of the workpiece in a state where the holding unit is brought relatively close to the peripheral edge inspection section.

In the invention, when visual inspection is performed, a workpiece is held by the holding unit, and inspection is performed while the holding unit is moved as needed. Moreover, when the peripheral edge inspection is performed, a workpiece is rotated while the workpiece is held by the holding unit without performing transfer of the workpiece, and the enlarged image of a peripheral edge of the workpiece is acquired in the peripheral edge inspection section.

Moreover, the invention provides a peripheral edge inspection unit mountable on the visual inspection apparatus including: an anchor that is detachable to a visual inspection section that allows visual inspection of the surface of a workpiece in a state where the workpiece is movably held by a holding unit; and an enlarged image acquisition part that is arranged so as to face a peripheral edge of the workpiece held by the holding unit, and is capable of acquiring an enlarged image of the peripheral edge of the workpiece.

In the invention, it is possible to fix the anchor to a predetermined position of the visual inspection section, thereby performing the peripheral edge inspection, using the holding unit of the visual inspection section. That is, visual inspection can be performed, without transferring a workpiece carried into the visual inspection section. Here, the peripheral edge refers to a side part, and a chamfered part of a workpiece, and a surrounding part of its front and back surfaces. Further, if the workpiece is a wafer, an edge cut line portion after an unnecessary resist is removed after application of a resist is included in the peripheral edge.

According to the present invention, in the visual inspection apparatus that has the visual inspection section that is used to allow visual inspection of the surface of a workpiece, the holding unit that holds the workpiece is shared by the visual inspection of the surface of the workpiece, and the peripheral edge inspection that inspects the peripheral edge of the workpiece. Thus, it is possible to perform the visual inspection and peripheral edge inspection while the workpiece is held by the holding unit, without performing transfer of the workpiece. Furthermore, compared with a case where apparatuses are configured independently, the installation area can be made small. Moreover, since the distance at which the workpiece is moved, and the time and effort for transfer can be omitted, the tact time of inspection can be reduced.

DETAILED DESCRIPTION OF THE INVENTION

Figure 2:
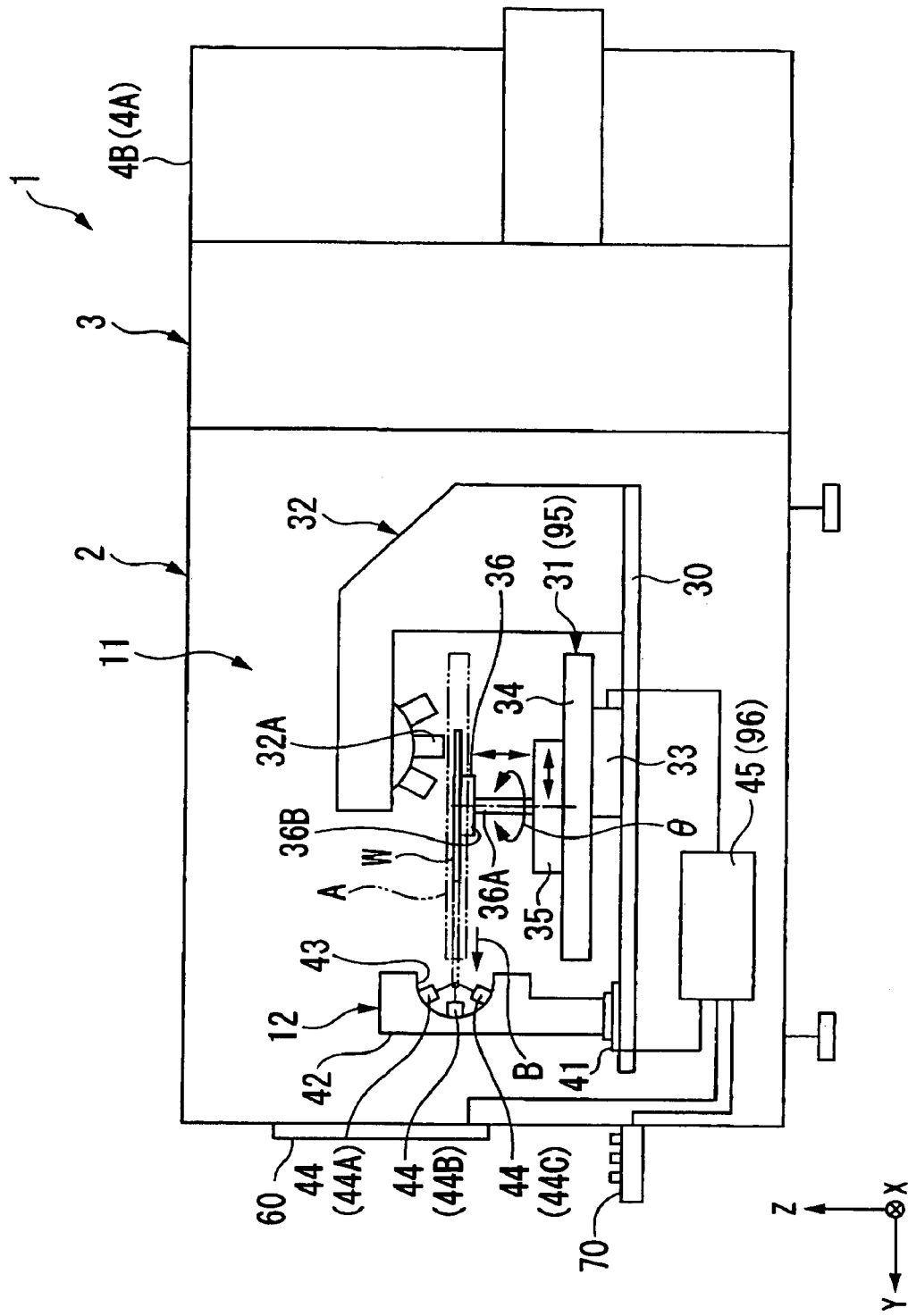
Figure 3:
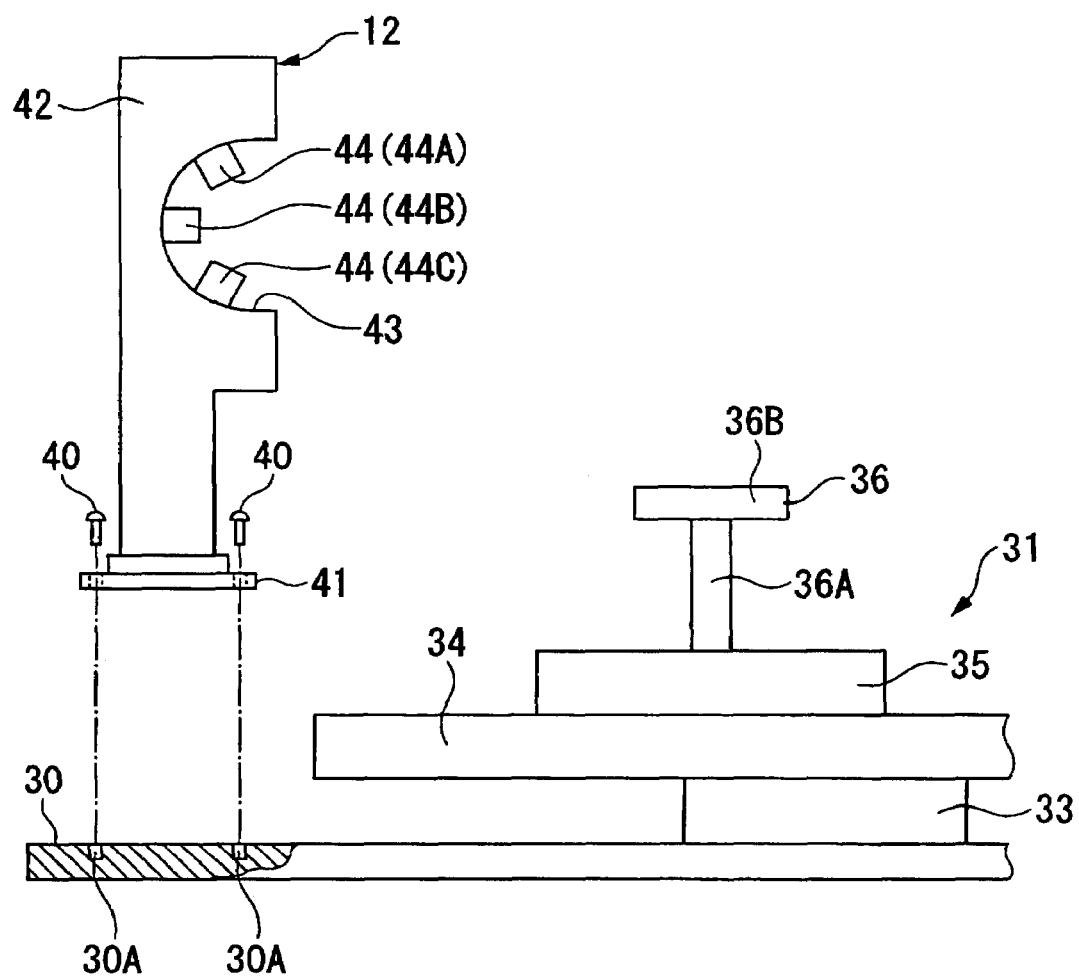
Figure 4:
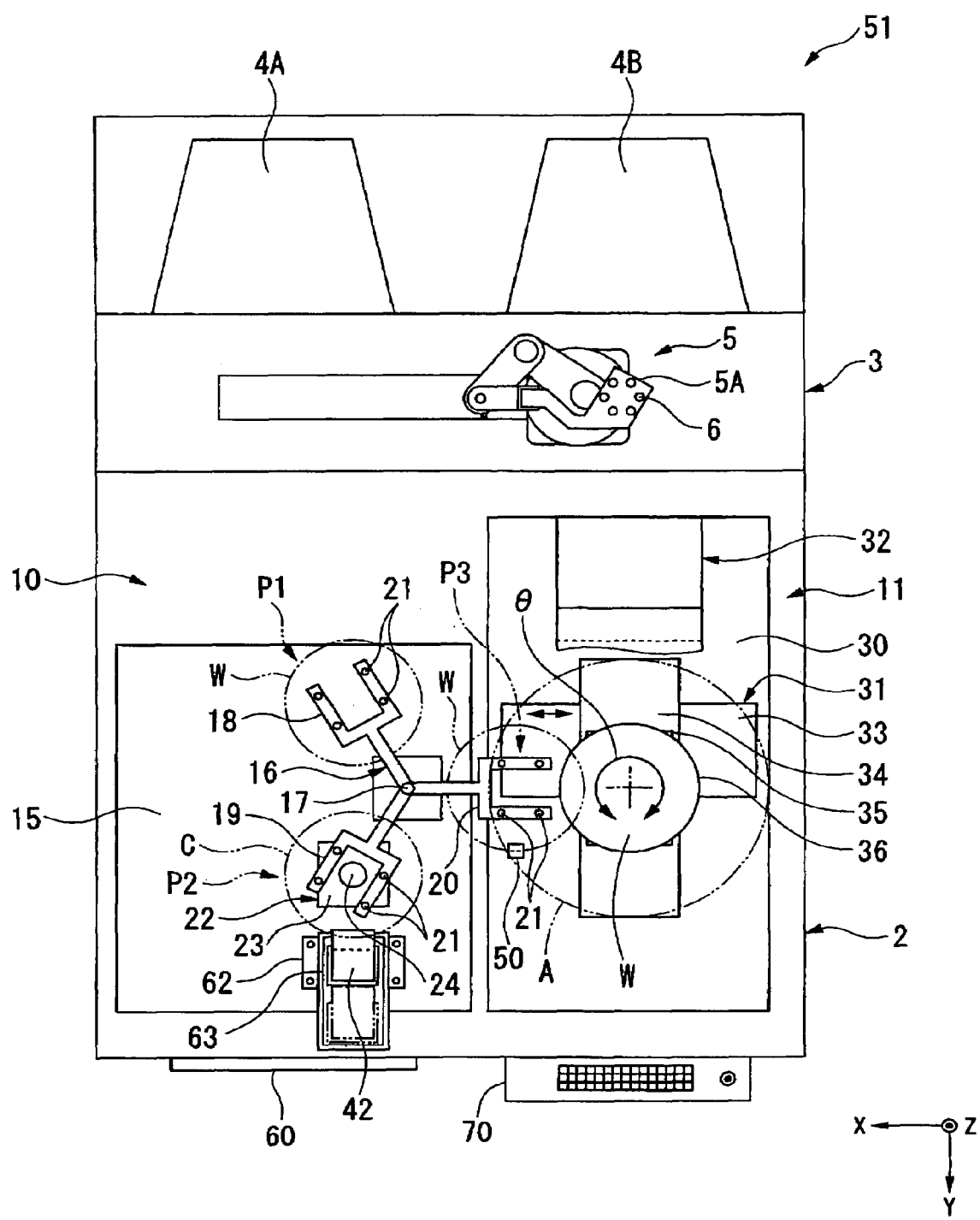
Figure 5:
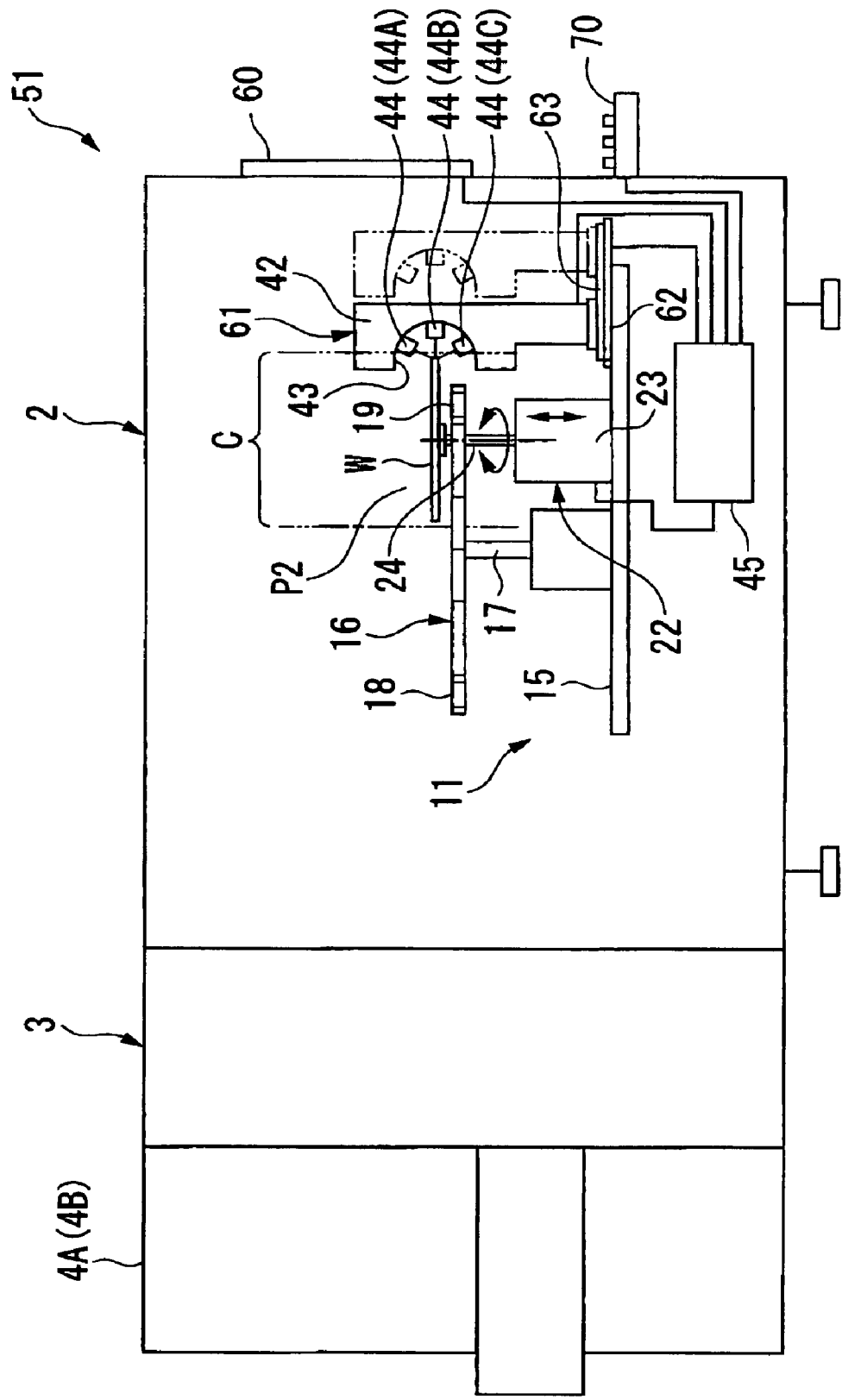
Figure 6:
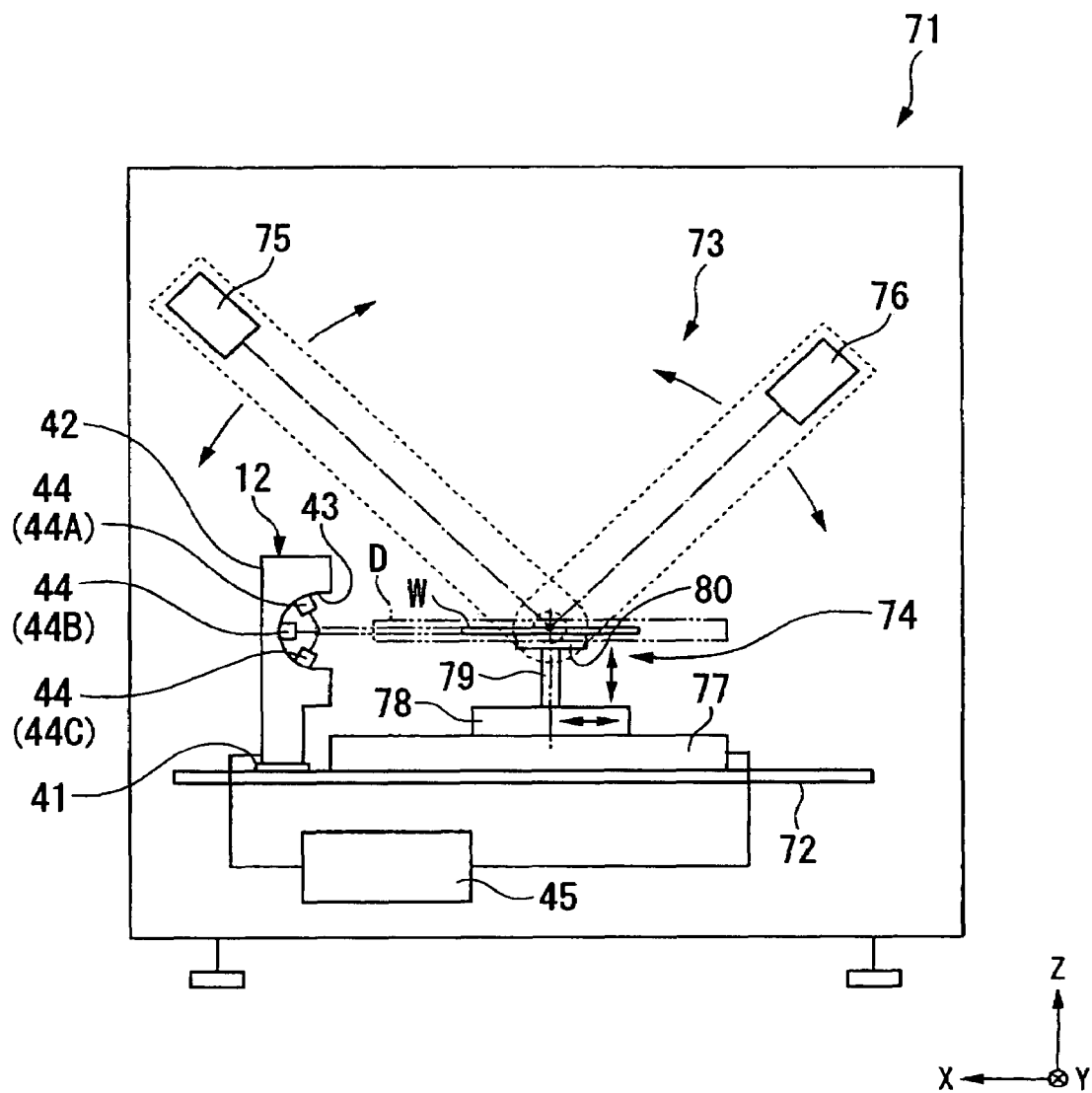
Figure 7:
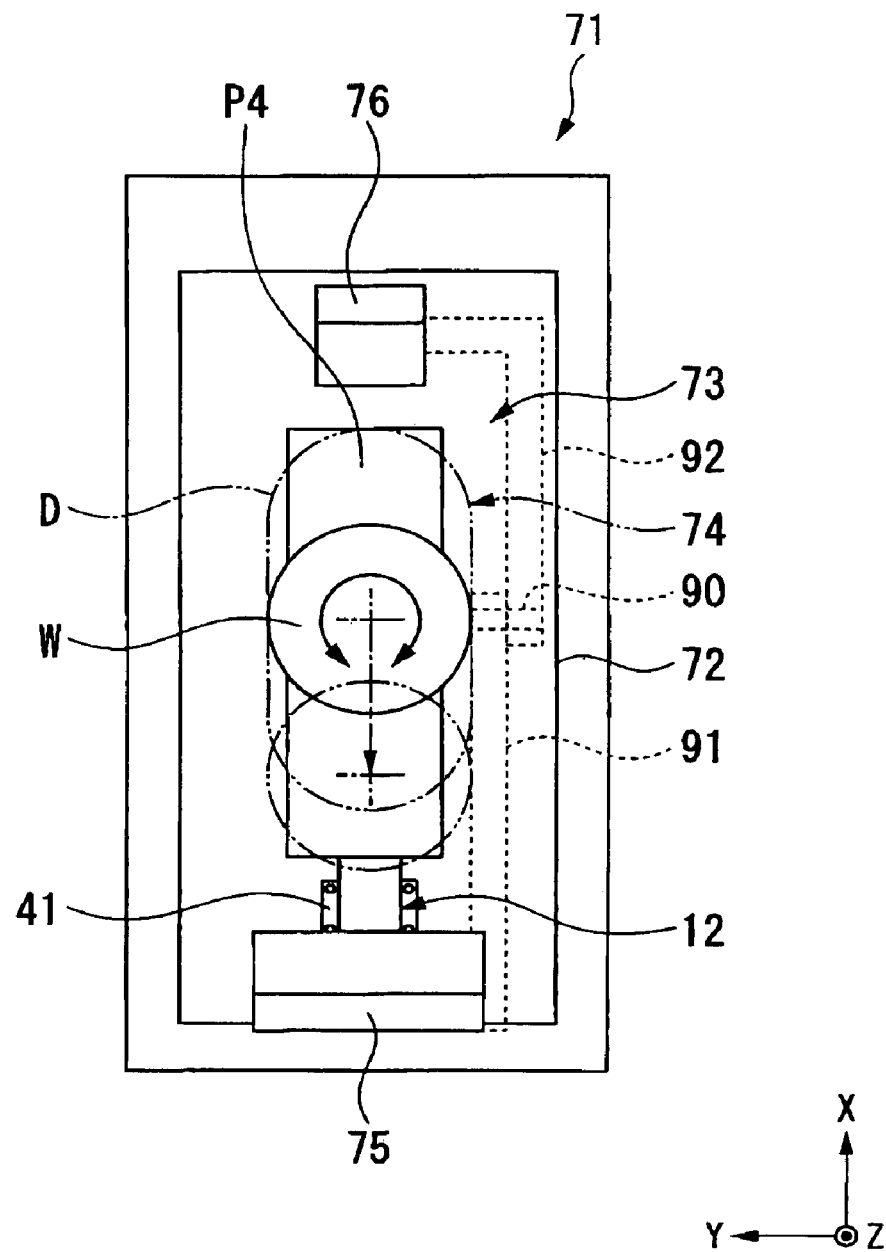
Figure 8:
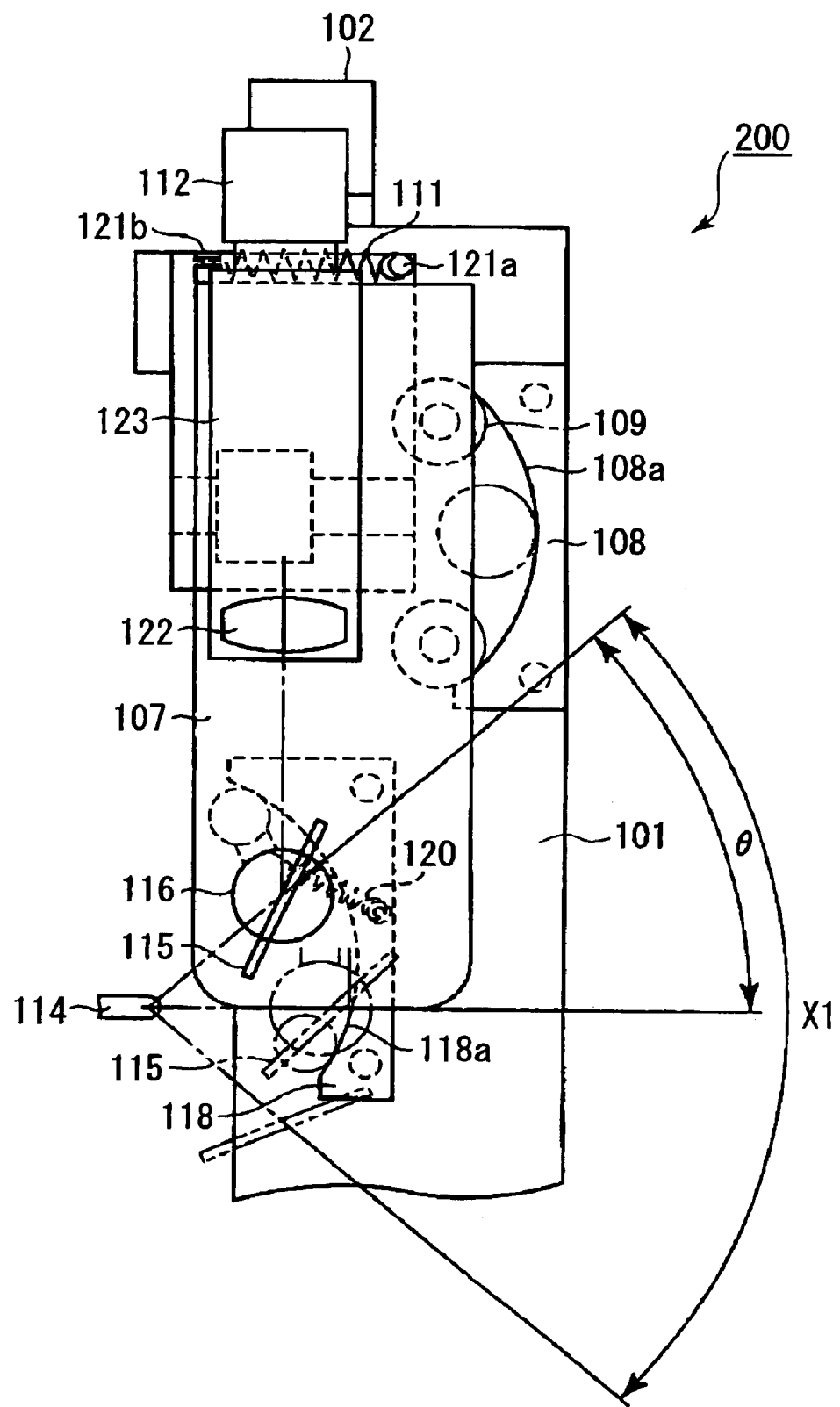
Figure 9A:
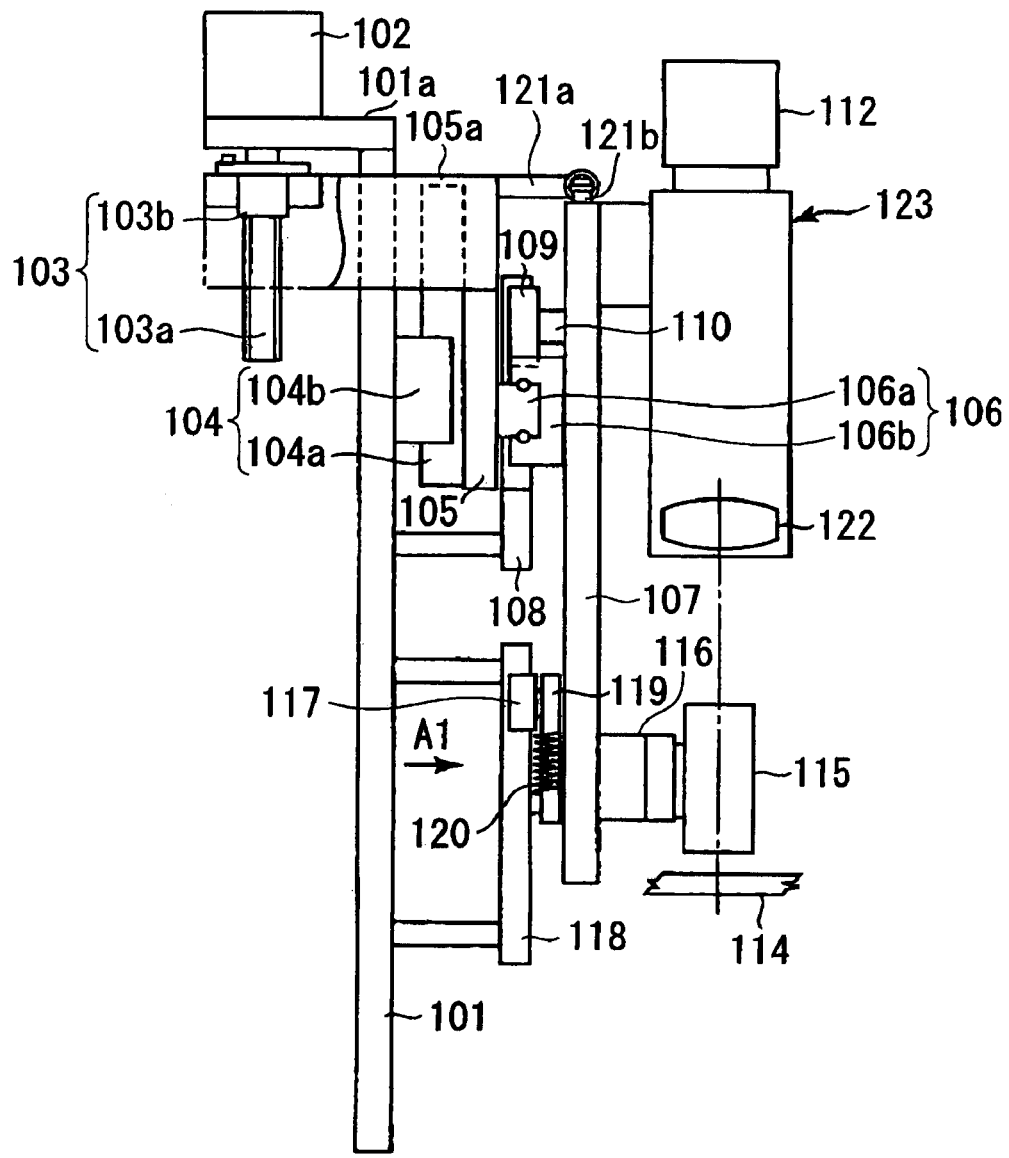
Figure 9B:
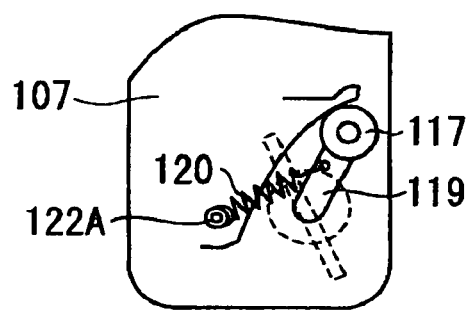
Figure 10A:
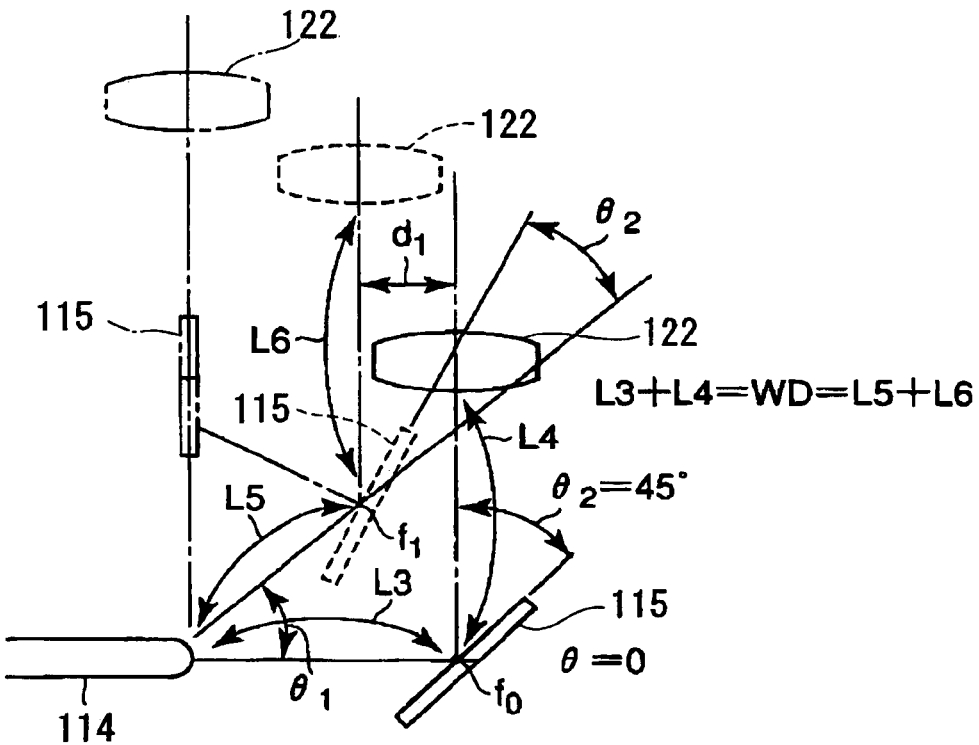
Figure 10B:
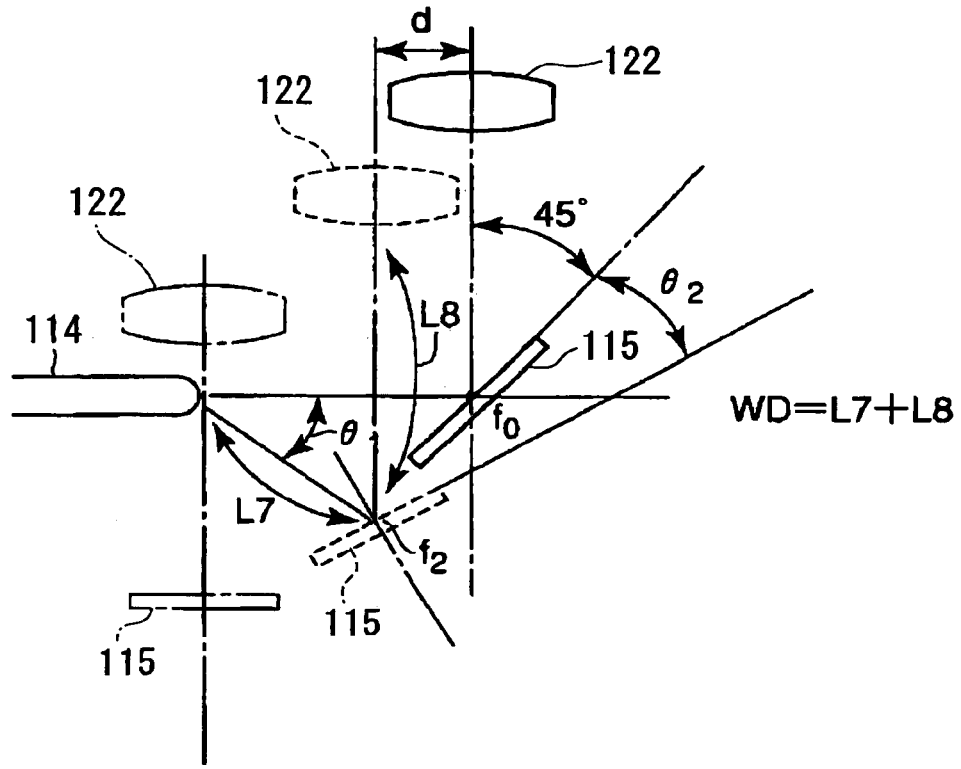
Figure 11:
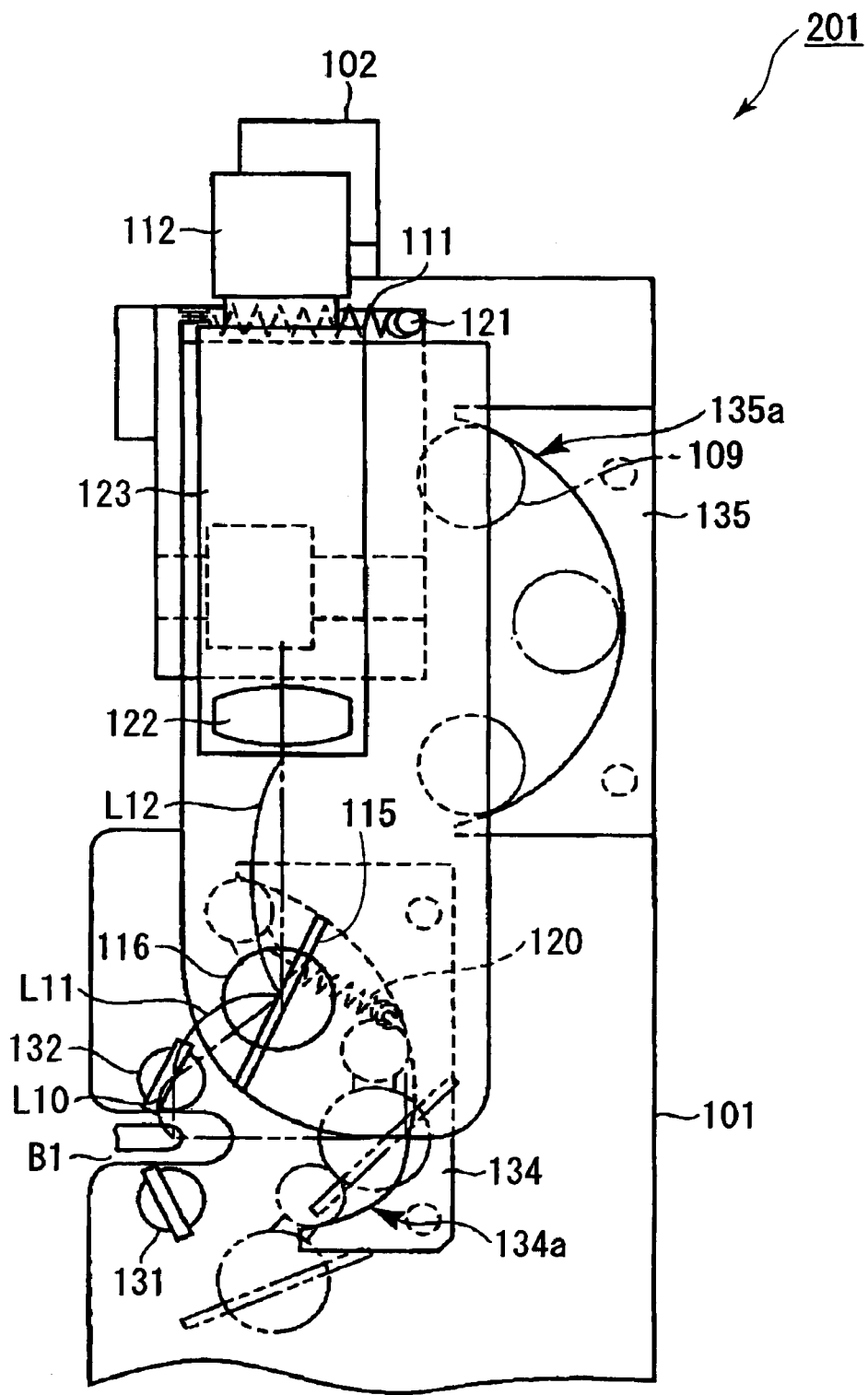
Figures 12A, 12B:
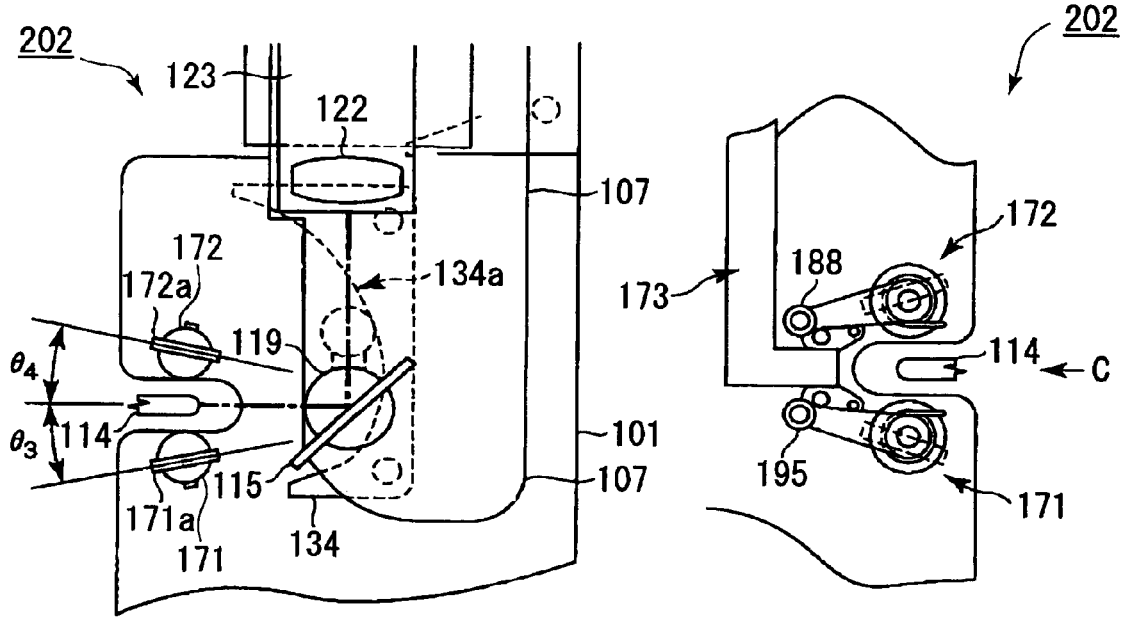
Figure 12C:
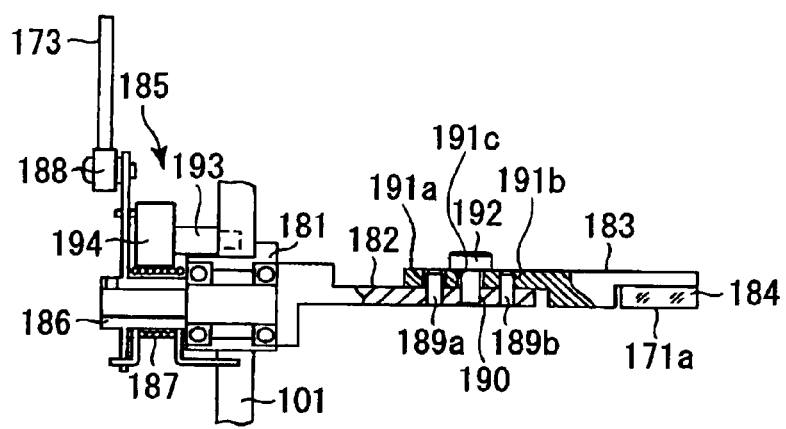
Figure 13A:
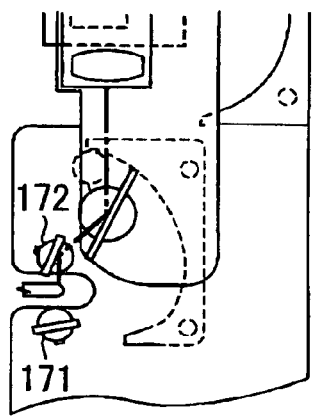
Figure 13C:
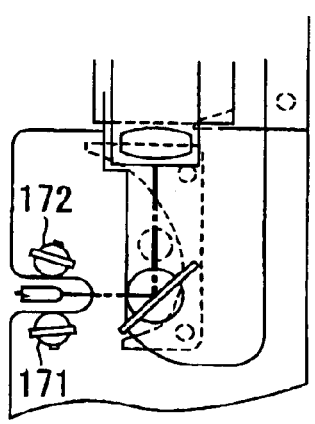
Figure 13F:
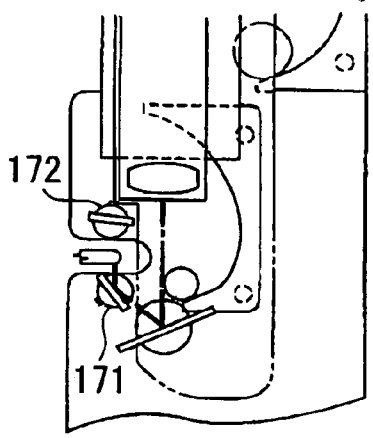
Figure 13B:
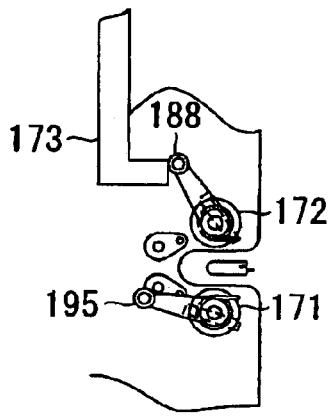
Figure 13D:
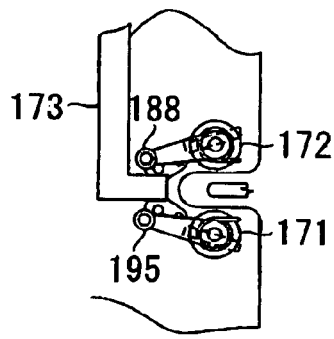
Figure 13G:
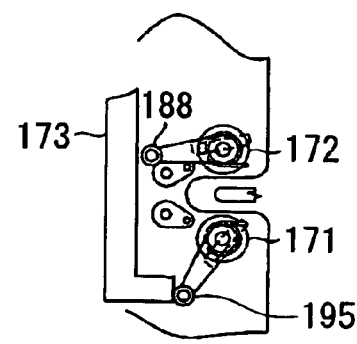
Figure 13E:
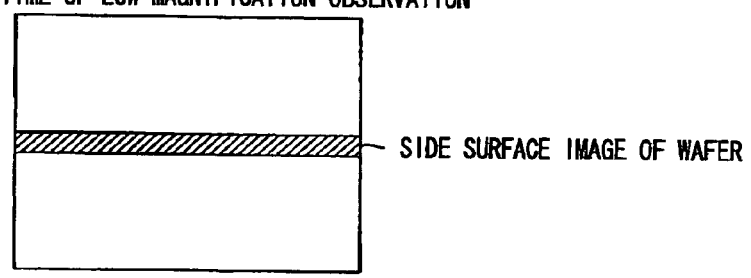

FIG. 1 is a plan view showing the schematic configuration of a visual inspection apparatus according to an embodiment of the invention FIG. 2 is a side view showing the schematic configuration of the visual inspection apparatus FIG. 3 is an exploded view illustrating attachment and detachment of a peripheral edge inspection section FIG. 4 is a plan view showing the schematic configuration of the visual inspection apparatus FIG. 5 is a side view showing the schematic configuration of the visual inspection apparatus FIG. 6 is a side view showing the schematic configuration of the visual inspection apparatus FIG. 7 is a plan view showing the schematic configuration of the visual inspection apparatus FIG. 8 is a view showing an exemplary configuration when a variable direction-of-view observation apparatus of a first mode is seen from the front of the apparatus FIG. 9A is a view showing an exemplary configuration when the variable direction-of-view observation apparatus of the first mode is seen from the side of the apparatus FIG. 9B is a view showing an exemplary configuration of a mirror cam as seen from an arrow A1 side in FIG. 9A FIG. 10A is a view for explaining an observable direction of view in the variable direction-of-view observation apparatus of the first embodiment FIG. 10B is a view for explaining the observable direction of view in the variable direction-of-view observation apparatus of the first embodiment FIG. 11 is a view showing an exemplary configuration when a variable direction-of-view observation apparatus of a second embodiment is seen from the front FIG. 12A is a view showing an exemplary configuration when a variable direction-of-view observation apparatus of a third embodiment is seen from the front FIG. 12B is a view showing an exemplary configuration when the variable direction-of-view observation apparatus of the third embodiment is seen from the back FIG. 12C is a view showing a cross-sectional exemplary configuration of a movable front-and-back observation mirror as seen from an arrow C1 side in FIG. 12B;

FIG. 13A is a view for explaining the operation of the variable direction-of-view observation apparatus of the third embodiment FIG. 13B is a view for explaining the operation of the variable direction-of-view observation apparatus of the third embodiment FIG. 13C is a view for explaining the operation of the variable direction-of-view observation apparatus of the third embodiment FIG. 13D is a view for explaining the operation of the variable direction-of-view observation apparatus of the third embodiment FIG. 13E is a view for explaining the operation of the variable direction-of-view observation apparatus of the third embodiment FIG. 13F is a view for explaining the operation of the variable direction-of-view observation apparatus of the third embodiment FIG. 13G is a view for explaining the operation of the variable direction-of-view observation apparatus of the third embodiment.

REFERENCE NUMERALS 1, 51, 71: VISUAL INSPECTION APPARATUS
10: MICRO-INSPECTION SECTION (VISUAL INSPECTION SECTION)
11: MICRO-INSPECTION SECTION (VISUAL INSPECTION SECTION)
12, 61: PERIPHERAL EDGE INSPECTION SECTION (PERIPHERAL EDGE INSPECTION UNIT)
15, 30, 72: LOADING PLATE
22: MICRO-INSPECTION UNIT (HOLDING UNIT)
31, 74, 95: INSPECTION STAGE (HOLDING UNIT)
36A, 79: ROTARY SHAFT
41: ANCHOR
44: ENLARGED IMAGE ACQUISITION PART
45, 96: CONTROL DEVICE
73: AUTOMATIC MICRO-INSPECTION SECTION (VISUAL INSPECTION SECTION)
W: WAFER (WORKPIECE)
101: BASE
101a: MOTOR ATTACHING PLATE
102: MOTOR
103: BALL SCREW SET
103a: BALL SCREW
103b: BALL SCREW GUIDE
104: Z-DIRECTION MOVABLE LINEAR GUIDE
104a, 106a: RAIL
104b, 106b: CASE
105: Z-MOVABLE CARRIAGE
105a: ARM
106: X-DIRECTION MOVABLE LINEAR GUIDE
107: X MOVABLE PLATE
108: CAM
108a, 118a: CAM SURFACE
109, 117: CAM ROLLER
111, 120: TENSION SPRING
112: CCD CAMERA
114: WAFER
115: ROTARY MIRROR
116: ROTARY SHAFT
118: MIRROR CAM
119: ROTARY ARM
121a, 121b: SPRING HOOK
122: IMAGING LENS
200, 201, 202: VARIABLE DIRECTION-OF-VIEW OBSERVATION APPARATUS (PERIPHERAL EDGE INSPECTION SECTION)

DETAILED DESCRIPTION OF THE INVENTION

The best modes for carrying out the invention will be described in detail with reference to the accompanying drawings.

FIRST EMBODIMENT

As shown in FIG. 1, a visual inspection apparatus 1 has an inspection section 2 provided at the front (a lower part in FIG. 1) that faces an inspector, and a loader part 3 is connected to the back side of the inspection section 2. In the loader part 3, two wafer carriers 4A and 4B that receive semiconductor wafers W (hereinafter referred to as "wafer W") that are workpieces are connected side by side. In addition, the wafer carriers 4A and 4B can receive a plurality of wafers W at a predetermined pitch in a vertical direction. For example, a non-inspected wafer W is received in the wafer carrier 4A, and an inspected wafer W is received in the wafer carrier 4B. Moreover, the wafer carriers 4A and 4B can be independently attached to and detached from the loader part 3.

The loader part 3 has an automated transport unit 5. The automated transport unit 5 includes a multi-segmented robotic arm, and a hand 5A at a tip of the robotic arm is provided with suction holes 6 that hold wafer W by suction-clamping. This automated transport unit 5 is configured movably and rotatably so that the wafer W can be transported between each of the two wafer carriers 4A and 4B and a macro-inspection section 10 of the inspection section 2.

The inspection section 2 has an the macro-inspection section 10 that is used in order for an inspector to inspect the surface of wafer W visually and macroscopically (macro inspection), and a micro-inspection section 11 that makes an inspection (micro inspection) performed by acquiring an image of the surface of wafer W as an enlarged image of a higher magnification than visual observation, and a peripheral edge inspection section 12 that acquires an enlarged image of a peripheral edge of wafer W is attached to the micro-inspection section 11.

In the macro-inspection section 10, a swivel arm 16 is rotatably and liftably provided on the loading plate 15. The swivel arm 16 has three transport arms 18, 19, and 20 horizontally extending equiangularly from a rotary shaft 17, and a plurality of suction holes (wafer chuck) 21 are provided at the tip of each of the transport arms 18, 19, and 20. These suction holes 21 are connected to a suction device that is not shown. Moreover, the rotation of the swivel arm 16 is controlled so that the transport arms 18, 19, and 20 may be arranged at positions P1, P2, and P3, respectively. The position P1 is a transfer position where wafer W is transferred between the macro-inspection section 10 and the loader part 3, and the position P2 is an inspection position where macro inspection is performed. The position P3 is a transfer position where wafer W is transferred between the macro-inspection section 10 and the micro-inspection section 11.

In addition, a macro-inspection unit 22 is provided in the position P2. The macro-inspection unit 22 has a base part 23 fixed to the loading plate 15. A holder 24 that holds wafer W by suction-clamping is provided in the base part 23 so as to be liftable and oscillatable in the Z direction (vertical direction), and causes the wafer W in the position P2 to rise towards an inspector so that the wafer W can be rotated and oscillated. Moreover, an illumination device (not shown) that illuminates wafer W in the position P2 is provided above the swivel arm 16. The illumination device is configured by, for example, a light source, and an optical system that can switch between irradiating a wafer W with illumination light as scattered light and irradiating the wafer W with the illumination light as condensed light. Further, a position detecting sensor 50 that make an alignment of a wafer W is provided in the position P3. This position detecting sensor 50 detects the position of a notch of the wafer W and any positional deviation of the center of the wafer W by rotating the wafer W while being placed on a rotating stage 36. If any positional deviation is detected, the position of the rotating stage 36 is corrected with the wafer W being lifted by the transport arms 18, 19, and 20 so that the rotation center of the rotating stage 36 and the rotation center of wafer W may coincide with each other, and thereafter, the transport arms 18, 19, and 20 are lowered to allow high-precision alignment.

As shown in FIGS. 1 and 2, the micro-inspection section 11 is installed on a loading plate 30 the vibration of which is removed by an appropriate vibration removal mechanism, and has an inspection stage 31 that is a holding unit that holds the wafer W, and a microscope 32 that observes the wafer W on the inspection stage 31. In the inspection stage 31, an X-axis slider 33 that is movable in the X direction shown in FIG. 1, and a Y-axis slider 34 that is movable in the Y direction are arranged so as to be stacked vertically. A Z-axis stage 35 that is movable in the Z direction is provided on the Y-axis slider 34. The Z-axis stage 35 is provided with the rotating stage 36 as a rotating mechanism that is rotatable in the θ direction. As shown in FIG. 2, the rotating stage 36 has a rotary shaft 36A connected with a motor that is not shown, and a holder 36B on a disk is fixed to an upper end of the rotary shaft 36A. The external diameter of the holder 36B is smaller than the external diameter of wafer W, and a central portion of the holder is provided with a suction hole (not shown) for sucking wafer W. The suction hole is connected to a suction device that is not shown.

Moreover, in the micro-inspection section 11, the peripheral edge inspection section 12 is fixed to a front side part of the loading plate 30. The peripheral edge inspection section has three enlarged image acquisition parts each including an imaging optical system, an imaging device, such as a CCD, etc., and captures an image of the peripheral edge of the wafer from its top, side, and bottom surface sides. Then, the captured image is displayed on a display unit 60, and is observed and inspected by an inspector. The peripheral edge inspection section 12 is located at a position that does not become obstructive when the surface of the wafer W is observed by the microscope 32 of the micro-inspection section 1, i.e., outside a micro-inspection region A shown by an imaginary line so as not to interfere with the wafer W at the time of micro-inspection. As shown in FIG. 3, the peripheral edge inspection section 12 is a peripheral edge inspection unit that can be freely detached and attached separately from the loading plate 30, and has an anchor 41 fixed to screw holes 30A of the loading plate 30 with bolts 40. A base part 42 extends in the Z direction from the anchor 41. A recessed part 43 is formed in this base part 42 so as to allow entrance of the peripheral edge of the wafer W. An enlarged image acquisition part 44 including a microscope that is a magnifying optical system, and a CCD (Charged Coupled Device) is provided in the recessed part. The enlarged image acquisition part 44 has an enlarged image acquisition part 44A that observes the upper surface (surface) of the peripheral edge of the wafer W from above, an enlarged image acquisition part 44B that observes the peripheral edge of the wafer W from the side, and an enlarged image acquisition part 44C that observes the lower surface (rear surface) of the peripheral edge of the wafer W from below. In addition, if the enlarged image acquisition part 44 has a configuration that can acquire an image, it will not be limited to the CCD. Further, the peripheral edge inspection sections 12 may have various configurations, such as a single-eye type including one enlarged image acquisition part 44 in a movable manner, and a five-eye type in which two enlarged image acquisition parts 44 are added so as to sandwich the enlarged image acquisition part 44B from the right and left. As an example of the single-eye type may include, a configuration in which the direction of an optical-axis is fixed, a microscope and a mirror that are movable relative to one another in the XYZ directions are included, and the mirror and the microscope are moved so as to keep the distance between the microscope and the part of an object to be observed always constant may be mentioned. This concrete configuration will be described below as a second modified example. Moreover, as another example of the single-eye type, a configuration in which only one enlarged image acquisition part 44 of the peripheral edge inspection section 12 of FIG. 3 is included, and an end of the wafer W rotates about the center thereof may be mentioned.

Also, as shown in FIG. 2, the inspection stage 31 and the peripheral edge inspection section 12 are connected to a control device 45. The control device 45 includes a CPU (Central Processing Unit), a memory, etc., and controls the whole visual inspection apparatus 1. In addition to these, the macro-inspection section 10, the automated transport unit 5, and a display device (not shown), such as a display, are also connected to the control device 45.

Next, the operation of the present embodiment will be described.

First, the wafer carrier 4A that has received the wafer W to be inspected, and the empty wafer carrier 4B is mounted on the loader part 3. The automated transport unit 5 takes out one wafer W from the wafer carrier 4A, and transfers the wafer to the transport arm 18 in the position P1 of the macro-inspection section 10. The swivel arm 16 rotates with the wafer W being held by suction-clamping by the transport arm 18, and moves the wafer W to the position P2. Here, after the wafer W is held and raised by the macro-inspection unit 22 after the suction of the transport arm 18 is released, the wafer W is made to rise, rotate, and oscillate by an oscillating mechanism.

When the surface of the wafer W has been irradiated with the illumination light from an illumination device, and the existence of a defect, or the state of the defect has been visually checked, the wafer W is lowered, and is again held by suction-clamping by the transport arm 18. In addition, at this time, the transport arm 20 is arranged in the position P1 by the rotation of the swivel arm 16. In this case, the following wafer W is placed on the transport arm 20 by the automated transport unit 5.

Next, the swivel arm 16 is rotated to move the wafer W in the position P2 to the position P3, and to move the wafer W in the position P1 to the position P2. Since the inspection stage 31 stands by in the position P3, the wafer W is transferred from the transport arm 18 to the holder 36B of the inspection stage 31. In addition, at this time, macro inspection is performed on the following wafer W that has moved to the position P2, similarly to the above. Further, still another wafer W is placed on the transport arm 19 that has moved to the position P1.

In the micro-inspection section 11, alignment of the wafer W is made in the position P2 on the rotating stage 36 of the inspection stage 31, the control device 45 makes the inspection stage 31 move, thereby making the part of the wafer W to be inspected move into the field of view of an objective lens 32A (refer to FIG. 2) of the microscope 32. An enlarged image acquired by the microscope 32 is visually checked as an inspector looks into an eyepiece that is not shown. Here, if an imaging device is installed in the microscope 32, inspection may be performed, visually observing the display unit 60. When micro inspection has been performed on all objects to be inspected while the inspection stage 31 is moved, the control device 45 makes the inspection stage 31 move obliquely forward in the XY direction as shown by the arrow B, thereby bringing the inspection stage 31 closer to the peripheral edge inspection section 12 and further malting the peripheral edge of the wafer W enter the recessed part 43 of the peripheral edge inspection section 12 while adjusting the height of the stage.

In the peripheral edge inspection section 12, for example, an image of the surface of the peripheral edge of the wafer W is acquired by the upper enlarged image acquisition part 44A, and the acquired image processed by the control device 45, is output to the display unit 60. In this case, the control device 45 makes the rotary shaft 36A of the inspection stage 31 rotate, thereby making the wafer W rotate in the θ direction at a predetermined speed. When the existence/non-existence of a scratch, etc. has been checked by performing single-around inspection of the peripheral edge of the wafer W in this way, then the peripheral edge inspection is performed similarly to the above by acquiring the images of the side surface and rear surface of the peripheral edge of the wafer W in order by the enlarged image acquisition part 44B and the enlarged image acquisition part 44C. In addition, the enlarged image acquisition parts 44A, 44B, and 44C may be operated at a same time, thereby simultaneously performing the inspections from three directions. Further, it is desirable that the inspection of the peripheral edge is automatically performed by image processing. For example, the luminance information of the peripheral edge of a good wafer W, and the luminance information of a wafer to be inspected that is acquired in advance may be compared with each other. Further, since the luminance of a peripheral edge of only one wafer W becomes constant except a notch, a portion the change of luminance of which has exceeded a fixed value may be extracted as a defect.

When the peripheral edge inspection has been completed, the inspection stage 31 is spaced apart from the peripheral edge inspection section 12, and is returned to the position P3 that is a transfer position, and is transferred to the transport arm 18 that stands by in the position P3. The swivel arm 16 rotates the transport arms 18, 19, and 20, and returns an inspected wafer W to the position P1. The automated transport unit 5 carries out the inspected wafer W, and receives the wafer W in the wafer carrier 4B. A non-inspected wafer W is newly transferred to the transport arm 18 in the position P1 that has become empty. Further, the next wafer W on which macro inspection has been performed in the position P2 is carried into the inspection stage 31 in the position P3. Then, when all wafers W as objects to be inspected within the wafer carrier 4A are inspected similarly to the above, the wafer carriers 4A and 4B are detached, and then the next wafer carriers to be inspected are mounted.

In addition, in this visual inspection apparatus 1, the shift to peripheral edge inspection is made after micro inspection is completed. However, the shift to micro inspection or peripheral edge inspection may be made with any timing by control of the control device 45. Moreover, only micro inspection and peripheral edge inspection may be performed without performing macro inspection, or only macro inspection and peripheral edge inspection may be performed without performing micro inspection.

According to the present embodiment, when visual inspection of the wafer W is performed, the peripheral edge inspection section 12 is attached to the micro-inspection section 11, and the inspection stage 31 of the micro-inspection section 11 is used for both the micro inspection and the peripheral edge inspection. Thus, the installation area of the apparatus can be made small. Moreover, the peripheral edge inspection can be performed without transferring the wafer W from the micro inspection, and the traveling distance of the inspection stage 31 can also be significantly reduced compared with the case where separate devices are provided. Thus, the takt time required for inspection can be shortened.

Since the peripheral edge inspection section 12 and the inspection stage 31 are configured so that they can relatively brought closer to or spaced apart from each other, it is possible to prevent the wafer W, etc. and the peripheral edge inspection section 12 from interfering with each other during micro inspection. Moreover, since the peripheral edge inspection section 12 and the inspection stage 31 are provided on the same loading plate 30, any deviation in the height direction becomes small, and the height adjustment at the time of peripheral edge inspection becomes easy. In particular, in the present embodiment, alignment is made with precision when the wafer W is transferred to the rotating stage 36. Thus, when wafer W is rotated and inspected in the peripheral edge inspection section 12, any movement caused by rotation of the wafer W in an observation position is suppressed, and an inspection at high magnification is allowed. Further, the position detecting sensor 50 detects the amount of deviation between the notch position and center position of the wafer W in the position P3. Thus, by controlling the inspection stage 31 at the time of inspection of a peripheral edge even if replacement of the wafer W is not performed, inspection may be performed in a state where any eccentricity is not caused when wafer W is rotated.

Further, the screw holes 30A that fix the peripheral edge inspection section 12 are bored in the loading plate 30 of the micro-inspection section 11, and the peripheral edge inspection section 12 is configured so as to be attachable to or detachable from the micro-inspection section 11 as a peripheral edge inspection unit. Thus, peripheral edge inspection can be performed only by mounting the peripheral edge inspection section 12 on a visual inspection apparatus having the macro-inspection section 10 and the micro-inspection section 11. That is, the aforementioned effects will be obtained even by the existing visual inspection apparatus only by its minimum changes. Alternatively, the peripheral edge inspection section 12 may be integrally anchored to the loading plate 30.

In addition, a uniaxial stage that is movable horizontally in the B direction may be provided between the anchor 41 of the peripheral edge inspection section 12, and the base part 42 so that the base part 42 can advance or retract in the direction of the wafer W. Even in this case, the same effects as the above can be obtained. Moreover, the takt time can be further reduced by moving the peripheral edge inspection section 12 towards the inspection stage 31. A stage that is interposed between the anchor 41 and the base part 42 is not limited to the uniaxial stage. For example, a biaxial stage that is movable even in a direction orthogonal to the B direction, a triaxial stage that is movable even in the Z direction, or a biaxial stage that is movable even in the B direction and the Z direction may be used satisfactorily. If the microscope 32 is configured such that the objective lens part 32A is movable in the Z-axis direction, and the base part 42 is configured so as to be movable in the Z direction, it becomes unnecessary to provide the inspection stage 31 with the Z-axis stage 35. Thus, the configuration of the inspection stage 31 can be simplified.

Further, the above embodiment may be modified so as to have a function to record the coordinate of an observation position when inspection is made in either one of the micro-inspection section and the peripheral edge inspection section and to move the observation position to an observation position of the other inspection section on the basis of the recorded coordinate of the observation position when inspection is made in the other inspection section (first modified example). That is, the first modified example, as shown in FIGS. 1 and 2, includes an inspection stage 95 that has a configuration similar to the inspection stage 31, and is adapted to be able to detect the coordinate of the position of the wafer W in each axial direction of XYZ, instead of the inspection stage 31 of the visual inspection apparatus 1 of the above first embodiment, and includes a control device 96 that has a configuration similar to the control device 45, and is adapted to be able to acquire and store the coordinate information on the position of a wafer detected by the inspection stage 95, and to control of visual inspection apparatus 1 using the coordinate information, instead of the control device 45.

The inspection stage 95 is mounted with, for example, a stepping motor, serving as a power source that drives the X-axis slider 33, the Y-axis slider 34, the Z-axis stage 35, and the rotating stage 36, which are provided similarly to the inspection stage 31, in their respective movement directions. Also, the coordinate of a position to which the wafer W has been moved can be detected on the basis of the information on the rotation angle of this stepping motor from its reference position.

Here, such as actuators, scales, which can detect the coordinates of a position, a servo motor, a linear scale, and a linear motor, other than the stepping motor, etc., can be suitably adopted as the power source of the inspection stage 95.

Next, the operation of the first modified example will be described.

While the wafer W put on the inspection stage 95 is moved and the peripheral edge of the wafer W is observed by the microscope 32 as micro inspection, in order to find out a defect and check the side surface or rear surface, the shift to peripheral edge inspection is immediately made so that the peripheral edge of the wafer W may be observed.

At that time, since the inspection stage 95 can detect coordinates in each axial direction, an instruction is issued by the operation part 70, like pushing one button, and the coordinate information is stored in the control device 96. Then, when the shift to peripheral edge inspection has been made from a point 97 on the optical axis of the objective lens of the microscope 32 that is performing the micro inspection, using the coordinate information stored in the control device 96, the inspection stage 95 is controlled by the control device 96 so that the point 97 observed by the microscope 32 can be observed as it is even by the peripheral edge inspection section, and thereby the wafer W is moved so that the point 97 may be located on the optical axis of the imaging optical system of the peripheral edge inspection section.

After the peripheral edge of the moved wafer W in various optional positions has been observed manually by the operation part 70 or automatically by an observation method that is input and set in advance, the shift to the original peripheral edge observation of the wafer W by the microscope 32 is made. Specifically, the coordinate information on the point 97 stored in the control device 96 is used to control the inspection stage 95, and the point 97 that has originally performed visual inspection of the peripheral edge of the wafer W by the microscope 32 is moved back to a position where it can be observed by the microscope 32.

On the contrary, when a defect is detected while the wafer W put on the inspection stage 95 is moved and the peripheral edge of the wafer W is observed in the peripheral edge inspection, in order to detect and check the defect by an enlarged image, the shift to the micro inspection by a microscope is immediately made so that the peripheral edge of wafer W may be observed.

In this case, the coordinates of the point 97 that is performing the peripheral edge inspection by an instruction by the operation part 70 is detected by the inspection stage 95, and the coordinate information is stored in the control device 96. Then, when the shift to micro inspection by a microscope has been made, the inspection stage 95 is controlled by the control device 96 so that the point 97 observed by the peripheral edge inspection section can be observed as it is even in the peripheral edge observation of the microscope 32, and thereby the wafer W is moved so that the point 97 may be located on the optical axis of the microscope 32.

After the peripheral edge of the moved wafer W in various optional positions is manually or automatically observed by the microscope, the shift to the original peripheral edge observation by the peripheral edge inspection section is made. Specifically, the coordinate information on the point 97 stored in the control device 96 is used to control the inspection stage 95, and the point 97 that has originally inspected the peripheral edge of the wafer W by the peripheral edge inspection section is moved back to a position where it can be observed by the peripheral edge inspection section.

Next, the effects of the first modified example will be described.

According to this modified example, if an attempt to observe the peripheral edge of a wafer as well as the surface of the wafer as it is or vice-versa is made while the wafer W put on the inspection stage 95 is moved, and the peripheral edge of the wafer W is observed by the microscope 32, that is, if any shift between the visual inspection and peripheral edge inspection is made, the coordinate information on the point that has been observed in each inspection is stored only by pushing one button of the operation part 70, and the wafer W is moved using the coordinate information. Thus, in each inspection, the same observation point can be observed. Therefore, for example, if a scratch, a crack, or the like that runs from the surface of a wafer to the peripheral edge and rear surface thereof is observed, the position of the scratch or crack can be observed continuously without any positional deviation, in the visual inspection and peripheral edge inspection by the microscope, observation precision and observation speed can be improved.

This makes it possible to smoothly and continuously perform visual inspection or peripheral edge inspection of the peripheral edge or other surfaces of the wafer W.

SECOND EMBODIMENT

A second embodiment is characterized in that the peripheral edge inspection section is provided in the macro-inspection section in which inspection is performed by visual observation. Other configurations and operations are the same as those of the first embodiment.

As shown in FIG. 4, in a visual inspection apparatus 51, a peripheral edge inspection section 61 (outer edge inspection unit) is detachably provided in the loading plate 15 of the macro-inspection section 10. The peripheral edge inspection section 61 has a anchor 62 fixed to the loading plate 15, a uniaxial stage 63, and a base part 42 attached to the enlarged image acquisition part 44. The base part 42 is attached so that it can be brought close to or spaced apart from the position P2. As shown in FIG. 5, in an inspection position where the base part 42 is brought closest to the position P2, the peripheral edge of the wafer W held horizontally by the macro-inspection unit 22 enter the recessed part 43. Further, as shown by an imaginary line, in a position when the base part 42 is most spaced apart from the position P2, the base part retracts from a macro-inspection region C, and will not interfere with the rotation of the swivel arm 16, and the oscillation of the wafer W by the macro-inspection unit 22.

Further, the macro-inspection unit 22 is a holding unit provided with a rotating mechanism that rotates the wafer W that is held while being oscillated, other than a lifting mechanism and an oscillation mechanism.

If visual inspection of the wafer W is performed in the present embodiment, the wafer W conveyed to the position P2 is held by suction-clamping by the macro-inspection unit 22, and is then macro-inspected. When the macro inspection has been completed, the wafer W is held horizontally at a predetermined height, and the peripheral edge inspection section 61 is moved to the inspection position. Then, while the wafer W is rotated by the macro-inspection unit 22, peripheral edge inspection is performed similarly to the first embodiment. When the peripheral edge inspection has been completed, the wafer W is transferred to the transport arm 19 from the macro-inspection unit 22 after the peripheral edge inspection section 61 retracts to a stand-by position. Further, the swivel arm 16 is rotated to transfer the wafer W to the position P3. From here, the wafer W is transferred to the micro-inspection section 1 where micro inspection is performed. When the micro inspection has been completed, the wafer W is returned to the position P1 via the position P3, and is then received in the wafer carrier 4B.

In addition, in this visual inspection apparatus 51, the shift to peripheral edge inspection is made after macro inspection is completed. However, the shift to macro inspection or peripheral edge inspection may be preferred at any timing by control of the control device 45. Moreover, only macro inspection and peripheral edge inspection may be performed without performing micro inspection, or only micro inspection and peripheral edge inspection may be performed without performing macro inspection.

In the present embodiment, the peripheral edge inspection section 61 is provided in the micro-inspection section 10, and the macro-inspection unit 22 of the micro-inspection section 10 is used for both the micro inspection and the peripheral edge inspection. Thus, the reduced installation area of the apparatus can be achieved. Moreover, the peripheral edge inspection can be performed without transferring the wafer W from the macro inspection, and the traveling distance of the peripheral edge inspection section 61 can also be significantly reduced compared with a case where separate devices are provided. Thus, the takt time required for inspection can be shortened. In addition, the effect obtained by providing the macro-inspection unit 22 and the peripheral edge inspection section 61 so that they can be brought close to or spaced apart from each other, and the effect obtained by loading the macro-inspection unit and the peripheral edge inspection section on the same loading plate 15 are the same as those of the first embodiment. Moreover, the effect obtained by configuring the peripheral edge inspection section 61 so as to be attachable to or detachable from the macro-inspection section 10 is the same as that of the first embodiment.

THIRD EMBODIMENT

A third embodiment is characterized in that the peripheral edge inspection section is provided in an automatic micro-inspection section that automatically extract a defect by image processing from an image captured by an imaging device.

Other configurations and operations are the same as those of the first embodiment. As shown in FIGS. 6 and 7, a visual inspection apparatus 71 has a loading plate 72 that is free from vibration, and an automatic micro inspection section 73 is constructed in the loading plate 72. The automatic micro-inspection section 73 has an inspection stage 74, and an illumination device 75 and an imaging section 76 fixed so as to sandwich the inspection stage 74 in the X direction. The inspection stage 74 includes an X-axis stage 77, a Z-axis stage 78, and a rotary shaft 79 serving as a rotating mechanism, and a holding plate 80 that holds a wafer by suction-clamping is fixed on the rotary shaft 79. The illumination device 75 has a line light source that irradiates the upper surface (surface) of the wafer W with linear illumination light from the slanting upper side. The line light source extends in the Y-direction orthogonal to the X-direction. Similarly, in the imaging section 76, an optical system is arranged so as to take an image of the linear reflected light or diffracted light that the illumination light from the illumination device 75 has been reflected by the upper surface of wafer W, and imaging devices are arrayed in a line in the Y-direction in the position of the image. Also, the optical axis of the imaging section 76 and the optical axis of the illumination device 75 are arranged so as to intersect each other on the upper surface of the wafer W. Also, the imaging section 76 and the illumination device 75 have rotation axes 90 on the lines on the wafer W that intersect each other, and are installed in rotatable members 91 and 92. As the imaging section 76 and the illumination device 75 rotate independently, an image can be taken at an angle suitable for various observation conditions, such as normal reflection, or plus/minus primary/secondary diffracted light.

Moreover, the peripheral edge inspection section 12 is fixed to the loading plate 72. The peripheral edge inspection section 12 is provided in a position where it has retracted from a macro-inspection region D of the wafer W shown by an imaginary line. In addition, the movable range of the inspection stage 74 in the X-direction is greater than the macro-inspection region D, and is such that the peripheral edge of wafer W can enter the recessed part 43 of the peripheral edge inspection section 12.

The operation of the present embodiment will now be described. The inspection stage 74 is made to stand by in a transfer position shown by a position P4, the wafer W is carried into the transfer position by a automated transport unit that is not shown, and the wafer W is held by suction-clamping in the inspection stage 74. Next, as the inspection stage 74 is moved in the X direction towards the peripheral edge inspection section 12, the linear illumination light from the illumination device 75 is reflected by the upper surface of wafer W, and is introduced into the imaging section 76 for each line, whereby the image of the whole wafer W is taken.

The control device 45 analyses a difference between an image captured by the imaging section 76, and a good image that is acquired in advance, and extracts as a defect a region whose luminance difference is more than a fixed value by image processing. Then, the position of the extracted defect, the information on size, and the classification information in that defects are automatically classified are registered in a storage unit for every wafer W.

When the automatic macroscopic inspection of wafer W has been completed, the inspection stage 74 is further moved in the X-direction so as to approach the peripheral edge inspection section 12, thereby making the peripheral edge of the wafer W enter the recessed part 43 of the peripheral edge inspection section 12. In that position, the wafer W is rotated in the θ direction, and peripheral edge inspection is performed similarly to the first embodiment. When the peripheral edge inspection has been completed, the rotation of the wafer W is stopped, and then returned to the position P4 where the wafer W is transferred.

In addition, in this visual inspection apparatus 71, the shift to peripheral edge inspection is made after automatic macro inspection is completed. However, the shift to macro inspection or peripheral edge inspection may be made at any timing by control of the control device 45. Further, when the automatic macroscopic inspection has been completed, the peripheral edge inspection section 12 may be arranged so that the peripheral edge of wafer W may enter the recessed part 43 of the peripheral edge inspection section 12. The illumination device 75 is arranged rotatably so that even if the peripheral edge inspection section 12 is arranged in such a position, such arrangement is allowed if it does not hinder the automatic macroscopic inspection. Moreover, the peripheral edge inspection section 12 may be configured so as to be movable in the X direction so that the peripheral edge inspection section 12 may be brought close to the wafer W after the completion of the automatic macroscopic inspection.

In the present embodiment, the peripheral edge inspection section 12 is provided in the automatic macro-inspection section 73, and the inspection stage 74 of the automatic macro-inspection section 73 is used for both the macro inspection and the peripheral edge inspection. Thus, the installation area of the apparatus can be made small. Moreover, the peripheral edge inspection can be performed without transferring the wafer W from the macro inspection, and the traveling distance of the inspection stage 74 can also be significantly reduced compared with a case where separate devices are provided. Thus, the takt time required for inspection can be shortened. Particularly if the inspection stage 74 is moved to make the peripheral edge of the wafer W enter the recessed part 43 of the peripheral edge inspection section 12, it is possible to achieve inexpensive manufacture by only making the inspection stage 74 extend in the X-direction. In addition, the effect obtained by providing the inspection stage 74 and the peripheral edge inspection section 12 so that they can be brought close to or spaced apart from each other, and the effect obtained by loading the inspection stage and the peripheral edge inspection section on the same loading plate 72 are the same as those of the first embodiment. Moreover, the effect obtained by configuring the peripheral edge inspection section 12 so as to be attachable to or detachable from the automatic macro-inspection section 73 is the same as that of the first embodiment.

In addition, the invention is not limited to the above respective embodiments, and can be applied widely.

For example, in the first embodiment, the installation position of the peripheral edge inspection section 12 is not limited to the position shown in FIG. 1, and may be attached to a side edge of the loading plate 30. In this configuration, it is possible to miniaturize a front part of the loading plate 30. Even in this case, the peripheral edge inspection section 12 is arranged so as to stand by in a position that does not become obstructive at the time of micro inspection.

There may be a visual inspection apparatus including only the micro-inspection section 11 and the peripheral edge inspection section 12 without having the macro-inspection section 10. Similarly, there may be a visual inspection apparatus including only the macro-inspection section 10 and the peripheral edge inspection section 12 without having the micro-inspection section 11. Further, there may be a visual inspection apparatus made up of an automatic micro-inspection section 73 and the micro-inspection section 11.

A recessed part that the peripheral edge of the wafer W can enter may be provided in the microscope 32, and the enlarged image acquisition part 44 may be arranged in the recessed part to form a peripheral edge inspection section. In this case, the space of the micro-inspection section 11 can be made much smaller. Further, as long as an arrangement space exists, a rotating stage and a peripheral edge inspection section may be provided in the position P1, and may be provided in the position P3.

The workpiece is not limited to a semiconductor wafer, and various workpieces, such as a glass substrate, may be used.

Further, a configuration including a variable direction-of-view observation apparatus to be described below can be adopted as the configuration of the above peripheral edge inspection section. This variable direction-of-view observation apparatus becomes a modified example (hereinafter referred to as a second modified example) including a concrete configuration of the example of the single-eye type of the above enlarged image acquisition part 44. In the following, as an example of the above workpiece, a wafer that is a flat plate-like test body will be described.

First, the concept of the variable direction-of-view observation apparatus of this modified example will be described.

As for the variable direction-of-view observation apparatus, for example, an example in which the device loaded into a microscope apparatus will be described.

As an embodiment of the variable direction-of-view observation apparatus of this modified example, an observation apparatus is used that has a flat plate made up of a wafer, etc. held as a test body (an observation object or a sample), and that is disposed in the vicinity of a stage of a microscope apparatus, which is movable and rotatable in triaxial directions orthogonal to one another, to observe the peripheral end face of the test body. For example, if a wafer is used as the (flat plate-like) test body, the optical axis of an observation optical system (for example, referred to as an imaging optical system) is arranged perpendicularly to the principal planes of the wafer. By rotating a rotary mirror that placed within the distance from a focus position uniquely possessed by the imaging optical system to an objective lens, i.e., WD (working distance), thereby changing the observation and installation direction (direction of view) of the test body, a mechanism that always keeps the distance between the objective lens accompanying the change of the direction of view and the test body at the above WD is given.

This modified example shows a basic configuration of visual inspection apparatus in which includes an optical system turntable (biaxial stage=ZX stage) on which an observation optical system and a rotary mirror are loaded, a turntable that moves the rotation of the mirror in the Z direction, and two cams that are engaged with the turntables.

The conceptual configuration of this modified example includes the following a, b, c, d, and e.

a. a biaxial stage that is movable in a direction (Z direction) orthogonal to the surface of a test body and a direction (X direction) parallel thereto;

b. a base having a driving unit that moves the biaxial stage in the Z direction;

c. an X-direction movable plate of the stage that includes an X-direction cam fixed to the base, a roller engaged with a cam attached in the X-direction movable plate of the biaxial stage, and a tension spring acting in a direction in which the base and the X-direction movable plate (X stage) are brought close to each other;

d. arranging on the X stage an observation (microscope) whose optical axis is adjusted at right angles to the surface of the test body, and a rotary mirror whose optical axis can be arbitrarily deflected between an objective lens of the microscope and the focus position of the lens as required; and e. having a mirror cam fixed to the base and a roller engaged with a cam attached to a rotary arm protruding from a rotary shaft of the rotary mirror, arranging a tension spring in a direction in which the roller is pressed against the cam between the rotary arm and a bar (spring hook) provided with the X-stage, and always making a focus on the end face of the test body by a drive of the base, even if the position of the observation optical system and the angle of the rotary mirror are changed by the cam, and the direction of view is moved.

Although this variable direction-of-view observation apparatus may be independently configured as an inspection (observation) apparatus, the apparatus is attached so that it can hold a wafer on a microscope apparatus for wafers as a test body, and can be disposed in the vicinity of a stage of the microscope apparatus, which is movable and rotatable in triaxial directions orthogonal to one another, to observe the peripheral end face of a test body held on the stage. Of course, the test body is not limited to the wafer, as will be described below. In addition, in the description explained below, a wafer is used as the test body, and a planar section in the front and back surfaces of the test body is called a principal plane. Further, the peripheral end face of a test body mainly refers to a non-planar peripheral edge of the front and back surfaces of a test body. Also, if chamfering, etc. is performed by machining, or if a resist that runs into a surrounding part of a partial rear surface called an edge cut line of a surface from which the resist of the peripheral edge is removed after application of a resist, the peripheral end surface also includes the above surrounding part.

Hereinafter, a first mode (hereinafter called a first mode for short) of this modified example will be described in detail.

FIGS. 8, 9A and 9B show an exemplary configuration of a first mode of a variable direction-of-view observation apparatus 200. Here, FIG. 8 is a view showing the exemplary configuration when the variable direction-of-view observation apparatus of the first mode is viewed from the front, FIG. 9A is a view showing the exemplary configuration when the variable direction-of-view observation apparatus of the first mode is viewed from the side, and FIG. 9B is a view showing an exemplary configuration of a mirror cam as viewed from the arrow A1 (back side of FIG. 8) in FIG. 9A.

The configuration of this variable direction-of-view observation apparatus 200 will be described. In addition, in the following description, a direction that is the same direction as the principal plane of a wafer used as a test body, and is orthogonal to the tangential line of an end face is defined as an X direction, and a direction that is orthogonal to the principal plane is defined as the Z direction.

A base 101 in the present apparatus is a plate-shaped member made of a metallic material, such as steel, aluminum, or stainless steel. The longitudinal direction of this base 101 is arranged in a direction orthogonal to the principal planes of the wafer 114 used as a test body.

A motor attaching plate 101a is attached to an upper end of the base 101 so as to project in the shape of the letter "L," and the motor attaching plate 101a is provided with a motor 102. A rotary shaft (not shown) of the motor 102 rotates in the X direction by a controller that is not shown. The rotary shaft of the motor 102 is connected with a ball screw 103a. The ball screw 103a is rotatably inserted and fitted into a ball screw guide 103b attached to an arm 105a extending from a Z-movable carriage 105 fixed to the base 101. The ball screw 103a and the ball screw guide 103b constitute a ball screw set 103. By this configuration, the ball screw 103a is moved by rotation of the rotary shaft of the motor 102 so as to push up or push down the ball screw guide 103b.

Further, a rail 104a that is fixed to the Z-direction movable carriage 105, and a case 104b that is slidably engaged with the rail 104a and fixed to the base 101 constitute a Z-direction movable linear guide 104.

Furthermore, a cam 108 in which a cam surface 108a that is curved in the shape of a recess is formed is fixed to an upper part of the base 101 via a plurality of struts. A mirror cam 118 in which a cam surface 118a is curved in the shape of a recess that is different from a cam surface 108a is fixed to a lower part of the base 101 via a plurality of struts.

Moreover, a rail 106a that is fixed to the Z-direction movable carriage 105, and a case 106b that is slidably engaged with the rail 106a and fixed to the X movable plate 107 constitute an X-direction movable linear guide 106. By this configuration, the Z-direction movable carriage 105 by the X-direction movable linear guide 106 and the X movable plate 107 by the Z-direction movable linear guide 104 can be moved two dimensionally in an X-Z plane.

Further, a cam roller 109 that moves while rotating along the cam surface 108a of the cam 108 is rotatably fixed to the X movable plate 107. A rotary shaft 116 is rotatably provided on the X movable plate 107. A rotary arm 119 is fixed integrally so as to extend from the rotary shaft 116. A cam roller 117 that moves along the cam surface 118a of the mirror cam 118 that functions as a rotation guide part is rotatably attached to the rotary arm 119. The rotary shaft 116 rotates by the movement of the cam roller 117 along the cam surface 118a.

A bar-shaped spring hook 121a is provided at an upper end of the base 101 on the cam 108 side, and a spring hook 121b is provided at the upper end of the X movable plate 107 opposite to the spring hook 121a. A tension spring 111 is hooked to the spring hooks 121a and 121b. The cam roller 109 acts so as to always push against the cam 108 by the biasing force of the tension spring 111. As shown in FIG. 9B, a tension sprig 120 is hooked between a hole of the rotary arm 119, and a spring hook 122A provided on the X movable plate 107. The cam roller 117 acts so as to always push against the cam surface 118a of the mirror cam 118 by the biasing force of the tension spring 120.

Furthermore, an imaging section 123 used as an observation optical system that has an optical axis in a direction orthogonal to the principal plane of a wafer in a state of being mounted on a rotary table is provided on the X movable plate 107. This imaging section 123 is made up of an imaging lens 122, and a CCD camera 112 that receives a light image that is focused on the imaging lens 122, and that generates image signals by photoelectric conversion. Of course, the imaging lens 122 may be a configuration made up of an objective lens and a lens that images an infinite luminous flux from the objective lens, like a microscope, or a single zoom lens may be used as the imaging lens. Further, a focusing mechanism or a zoom variable power mechanism may be electrically driven. A rotary mirror 115 that deflects the optical axis of the imaging lens 122 exists within the WD of the imaging lens, and is bonded to the rotary shaft 116 attached to the X movable plate 107.

The operation of the variable direction-of-view observation apparatus 200 loaded on the microscope apparatus configured in this way will be described.

The fact that this apparatus always comes into focus even if the direction of view is changed to the end face of a wafer in the following order (even if the rotary mirror is rotated) will be described.

First, referring to FIG. 8, according to an instruction from an inspector (observer), the motor 102 will be rotated by control of a controller that is not shown. By this rotation, the ball screw 103a is also rotated and moved so as to push up or push down the ball screw guide 103b. If the ball screw is moved so as to push down the ball screw guide, the Z movable plate 105 is moved so as to approach the wafer 114 along the guide direction of the Z-direction movable linear guide 104.

During this decent, the Z movable plate 105 is moved rightward along the cam surface 108a such that the cam roller 109 is pushed against the cam 108 by the biasing force of the tension spring 111. Simultaneously with this the rotary arm 119 is also moved such that the cam roller 117 is pushed against the cam surface 118a of the mirror cam 118 by the spring 120. If the cam roller 117 is moved along the cam surface 118a, the rotary arm 119 will rotate in the clockwise direction.

That is, while the imaging lens 122 descends so as to approach a wafer 114 along the Z direction (the direction of an optical axis), it moves in the X direction so as to separate from an end of the wafer 114 in the direction of a principal plane thereof. In other words, as shown in FIG. 8, the end of the wafer 114 and the rotary shaft 116 descend at an equal distance (WD). At this time, as the rotary arm 119 rotates in the clockwise direction, the rotary mirror 115 also rotates in the clockwise direction. That is, the shape of the cam surface 118a is designed such that the optical axis of the imaging lens 122 is deflected by the rotary mirror 115, the optical axis always coincides with the end face of the wafer 114, and the distance WD from the imaging lens is kept constant via the end face and the rotary mirror.

As a result, even if the angle ($\theta$) at which the end face of the wafer 114 is observed is changed, a situation where the imaging lens 122 is always focused on the end face of the wafer can be created. In this regard, in the present embodiment, the direction of view that allows observation is preferably set to about ±45 degrees to the principal planes of the wafer 114. Substantially, this is because, if the deflection angle of the rotary mirror 115 is approximately parallel to the optical axis of the imaging lens 122, the reflecting surface (mirror surface) of the rotary mirror 115 should be extremely increased, and therefore, there is an actual limit to the area of the reflecting surface of the mirror.

The reason for this will be briefly described with reference to FIGS. 10A and 10B.

As shown in FIG. 10A, the positional relationship between the imaging lens 122 and the rotary mirror 115 ($\theta_2 = 45°$) when the observation from the same direction ($\theta = 0$) as the principal planes of the wafer 114 is started is shown by a solid line, and the positional relationship between the imaging lens 122 and the rotary mirror 115 when an end face is observed from above is shown by a broken line.

When $\theta$ is $\theta_1$, $\theta_2$ is expressed as $\theta_2 = (\frac{1}{2}) * \theta_1$. Consequently, when $\theta$ increases, $\theta_2$ also increases, and thus the reflecting surface coincides with the optical axis as indicated by a one-dotted chain line, which will hinder the observation. Similarly, as shown in FIG. 10B, when the observation from below the wafer 114 is made, part of the wafer 114 may enter a space between the imaging lens 122 and the rotary mirror 115, which will interfere with the observation.

Further to describe, the optical axis of the imaging lens 122 will be most separated from the end face of the wafer 114 when $\theta = 0$. It can also be appreciated that, as $\theta$ becomes large, the optical axis approaches the wafer 114. Consequently, the mirror cam 118 is designed in consideration of these points.

As described above, according to the variable direction-of-view observation apparatus 200 of the first mode of this modified example, the rotary mirror 115 is moved in a direction (Z direction) orthogonal to a principal plane with respect to the peripheral end face in the test body 114 having two principal planes, such as a wafer, while a substantially constant distance is kept from the peripheral end face of the test body 114. Therefore, the distance WD (working distance) to the peripheral end face and the observation optical system becomes constant. As a result, while the end face is observed (imaged), the end face of the test body can always be focused.

Further, since the X movable plate that is supporting the imaging section 123 is moving in the direction of the principal planes of the wafer 114 only to such an extent that the distance WD is kept, the variable direction-of-view observation apparatus of the present embodiment is miniaturized. Further, the inspection apparatus is not necessarily made up of a single unit, and can be disposed and used in the vicinity of a stage of a conventional microscope apparatus that holds a test body and is movable and rotatable in triaxial directions orthogonal to one another. Of course, the observation apparatus can also be loaded onto other apparatuses including a stage, without being limited to the microscope apparatus for a wafer.

Moreover, various test bodies can be observed by suitably focusing the curved state of the peripheral end face of the cam surface 108a, 118a in the cam 108, 118 to the shape of a peripheral end face of a test body to be observed. For example, the cam 108, 118 may be detachably configured so that it can be suitably replaced according to a test body. As a result, even if the cross-sectional shape of an end face of a test body is a sufficiently rounded shape or a shape the corner of which is slightly rounded, focusing in the imaging section can be made easily.

By providing the peripheral edge inspection section 12 of the visual inspection apparatus 1 of the above embodiment with such a variable direction-of-view observation apparatus 200, observed images of the end face of the wafer 114 and its front and back surfaces following the end face are led to a microscope of the peripheral edge inspection section 12, so that chips or cracks generated in the end face of the wafer can be detected. Further, in the case of inspection of a mask pattern, the edging state of a resist film, deposition of chemical solution used for forming the resist onto the rear surface of a wafer, etc. can be inspected.

Next, with reference to FIG. 11, an exemplary configuration of a variable direction-of-view observation apparatus of a second mode (hereinafter called a second mode for short) of this modified example will be described. In addition, the constituent parts shown in FIG. 11 equivalent to the aforementioned constituent parts shown in FIGS. 8, 9A and 9B are denoted by the same reference numerals, and the description thereof is omitted. While the aforementioned first mode has a limit to the observation angle (about ±45 degrees), the present mode is an example in which observation is performed right above or right below a test body. In the present mode, observation of front and back sides of an outer peripheral part of a test body is allowed by further providing two front-and-back observation mirrors as shown in FIG. 11.

In this variable direction-of-view observation apparatus 201, a notch B1 is formed in the base 130, and this notch is configured so as to allow entrance of an end of the wafer 114. Moreover, when the end of the wafer 114 is inserted into the notch B1, front-and-back observation mirrors 131 and 132 fixed to the upper and lower parts, respectively, on the optical axis (direction orthogonal to the principal plane of the wafer 114) are arranged in the positions that recede slightly inward from the end of the wafer.

When observation of an upper principal plane of the wafer 114 is taken as an example, the optical axis in the imaging lens 122 will become the same as an optical axis deflected by the front-and-back observation mirror 131 if the inclinations of the rotary mirror 115 and the front-and-back observation mirror 131 are made equal to each other. That is, since the optical axis curved by these front-and-back observation mirrors 131, 132 is orthogonal to each principal plane of the wafer 114, it is consequently possible to observe front and back sides of the outer peripheral part of the wafer 114.

In such an arrangement, a cam surface 135a that extends so as to make the optical axis from a front-and-back observation mirror coincide with the optical axis of an imaging lens is provided in a cam 135 in correspondence with the cam profile in the aforementioned first mode. By providing the cam surface 135a, the angle of a rotary mirror can be determined so as to make an optical axis coincide with the optical axis of an imaging lens, in relation to the angle of a front-and-back observation mirror. The shape of a cam surface 134a is similarly given to a cam 134 so that the sum of L10, L11, and L12 may be equal to WD. In addition, when WD is not completely equal to the sum due to any individual difference of the wafer 114, etc., it is also possible to cope with this by interposing a stop so as to give a sufficient depth of field to an observation optical system or by installing an AF (automatic focusing) device.

Alternatively, although a wafer is exemplified as a test body used as an observation object by the variable direction-of-view observation apparatus of this modified example, the invention is not limited thereto. For example, by loading a glass substrate used for a liquid crystal display panel onto an inspection apparatus for the glass substrate, it is also possible to observe an end face of the glass substrate. Furthermore, the end face of a cut product can also be observed by attaching the product to a metal cutting apparatus.

As described above, according to the aforementioned first and second modes, it is possible to observe the peripheral end face of a wafer used as a test body from a desired angle, and it is possible to simply observe damage, such as chips or cracks generated in the end face and front and back surfaces over the whole outer periphery of the wafer, or adhering foreign matters, without carrying out focusing work each time. Further, even in this second mode, it is possible to easily attach the observation apparatus to a microscope apparatus similarly to the aforementioned first mode, and load it into a wafer visual inspection apparatus, a wafer inspection apparatus, etc. Alternatively, the observation apparatus may be provided in a substrate processing apparatus that has rotating stages, such as an exposure apparatus, a coater, and a developer.

Next, a variable direction-of-view observation apparatus of a third mode (hereinafter called a third mode for short) of this modified example will be described in detail.

In the aforementioned second mode, the front-and-back observation mirrors 131 and 132 are fixed and are turned to a fixed direction regardless of the angle of the rotary mirror 115. Therefore, if low magnification observation is set when the end face of the wafer 114 is observed by the rotary mirror 115, the front-and-back observation mirrors 131 and 132 may enter the field of view of observation of the rotary mirror 115. This mode is an exemplary configuration in which, when a movable front-and-back observation mirror is provided to observe the end face of a test body, the observation mirror is made to remove from the field of view of observation of the rotary mirror 115.

FIG. 12A is a view showing the exemplary configuration when the variable direction-of-view observation apparatus of the third mode is viewed from the front, FIG. 12B is a view showing the exemplary configuration when the variable direction-of-view observation apparatus of the third mode is viewed from the back, and FIG. 12C is a view showing an exemplary configuration of a movable front-and-back observation mirror as viewed from the arrow C1 in FIG. 12B. In addition, the constituent parts shown in FIGS. 12A, 12B, and 12C equivalent to the aforementioned constituent parts shown in FIGS. 8 and 9 are denoted by the same reference numerals, and the descriptions thereof is omitted.

As shown in FIG. 12A, a variable direction-of-view observation apparatus 202 is provided with movable front-and-back observation mirrors 171, 172 so that, when the rotary mirror 115 observes the end face of the wafer 114, mirror surfaces 171a, 172a may be in specified positions that have depression angles (direction converged on the rotary mirror 115 on the basis of the direction of an optical axis of the imaging lens 122) of arbitrary angles $\theta_3$, $\theta_4$ with respect to the rotary mirror 115 on the basis of the principal planes of the wafer 114. The arbitrary angles $\theta_3$, $\theta_4$ are angles provided to prevent the outside light (illumination light, etc.) reflected by the wafer 114 from being reflected again by the movable front-and-back observation mirrors 171, 172, and entering the rotary mirror 115. The arbitrary angles $\theta_3$, $\theta_4$ incline slightly with respect to the front and back principal planes of the wafer 114, and are provided so as to have a depression angle (an elevation angle with respect to a wafer principal plane) with respect to the rotary mirror 115.

These movable front-and-back observation mirrors 171, 172 have the same configuration, and as shown in FIG. 12B, they are arranged axisymmetrically to the wafer 114 (the direction of an optical axis). Between these movable front-and-back observation mirrors 171, 172, a driving plate 173 is provided that is fixed to the X movable plate 107 shown in FIG. 9, and rotates any one of the movable front-and-back observation mirrors 171, 172 along with vertical movement of the driving plate.

Next, a configuration will be described taking the movable front-and-back observation mirror 171 as an example.

As shown in FIG. 12C, the movable front-and-back observation mirror 171 includes; a mirror body 182 that is rotatably attached to the base 101 by fitting a bearing 181 thereinto, a mirror base 183 replaceably attached to the mirror body 182, a mirror 184 fixed to a tip (the lower side in this drawing) of the mirror base 183, a stopper part 185 provided to specify the aforementioned specified position in the base 101, a lever part 186 that is connected and fixed to the mirror body 182 via the bearing 181, a cam 188 that is provided at the tip of the lever part 186 to rotate the mirror body 182 along with the vertical movement of the driving plate 173, and a coil spring 187 that applies a biasing force that is required for the mirror body 182 to return to a specified position.

As a configuration in which the mirror base 183 is attached to the mirror body 182, an attachment surface m of the mirror body 182 is provided with at least two pins 189a and 189b and a screw hole 190, and holes 191a and 191b that are fitted to the pins 189a and 189b, and a screw hole 191c are formed in the mirror base 183, respectively.

As for the attachment, after the holes 191a and 191b of the mirror base 183 are respectively fitted to the pins 189a and 189b of the mirror body 182, a screw 192 is screwed into the screw hole 190 through the screw hole 191c. As such, since the mirror base 183 has a detachable configuration, even if a mirror becomes dirty, it can be easily cleaned.

The stopper part 185 includes a stopper column 193 fixed to the base 101, and a stopper 194 that defines a specified position where the lever part 186 is locked. The coil spring 187 has one end hooked to the lever part 186, and the other end hooked to the base 101, and the biasing force of the coil spring is applied so that the lever part 186 may always be pressed against the stopper 194.

Next, with reference to FIGS. 13A to 13G, the operation of the movable front-and-back observation mirrors 171, 172 configured in this way will be described. In this example of observation, the lower surface of a wafer is observed via an end face from the upper surface of the wafer.

FIG. 13A shows a state where the upper surface of the wafer 114 is observed from the front of the apparatus, and FIG. 7B shows the rotational state of the movable front-and-back observation mirrors 171, 172 viewed from the back. In this observation state, the rotary mirror 115 is located higher than the movable front-and-back observation mirror 172, and the cam 188 of the movable front-and-back observation mirror 172 is pulled up by the driving plate 173. Then, the front surface (upper principal plane) of the wafer projected on the movable front-and-back observation mirror 172 is projected via the rotary mirror 115 so as to run along the optical axis of the imaging lens 122. At this time, the movable front-and-back observation mirror 171 is in a free state, is biased by the coil spring 187, and is held at the arbitrary angle $\theta_3$ so that the surface of the mirror may be in the aforementioned specified position.

Moreover, when a peripheral end face of the wafer 114 is observed from a direction substantially vertical to the normal line of a surface of the wafer from the state shown in FIGS. 13A and 13B, the rotary mirror 115 is pressed down while rotating, resulting in the observation of the end face of the wafer 114 (refer to FIGS. 13C and 13D). In the state where this end face is observed, the cams 188, 195 of the movable front-and-back observation mirrors 171, 172 are not in contact with the driving plate 173, but in a free state. For this reason, the movable front-and-back observation mirrors 171, 172 are together in a free state, are biased by the coil spring 187, and are held at the arbitrary angles $\theta_3$, $\theta_4$ so that the surface of the mirror may be in the aforementioned specified position.

At this time, as shown in FIG. 13E, the mirror 184 of the movable front-and-back observation mirror 171, 172 is put into rotation, so that it cannot enter the field of view of observation of the rotary mirror 115.

In this observation state, the rotary mirror 115 is pushed down while rotating, and is thereby located lower than the movable front-and-back observation mirror 171, and the cam 195 of the movable front-and-back observation mirror 171 is pulled down by the driving plate 173. Then, the rear surface of the wafer (lower principal plane) projected on the movable front-and-back observation mirror 171 is projected via the rotary mirror 115 so as to run along the optical axis of the imaging lens 122. At this time, the movable front-and-back observation mirror 172 is in a free state, is biased by the coil spring 187, and is held at the arbitrary angle $\theta_3$ so that the surface of the mirror may be in the aforementioned specified position (refer to FIGS. 13F and 13G).

As described above, according to this mode, by rotating one of two movable front-and-back observation mirrors that are arranged vertically, with movement of a rotary mirror, an observed image of the front surface or rear surface of a test body can be guided to the optical axis of an imaging lens by the rotated movable front-and-back observation mirror and the rotary mirror. Further, when the end face of a test body is observed, both the movable front-and-back observation mirrors are retracted from a field of view of observation. It is therefore possible to provide an easily viewable observation image in which only the test body used as an observation object exists within a field of view of observation. Further, even in this third mode, it is possible to easily attach the observation apparatus to a microscope apparatus similarly to the aforementioned first mode, and load it into a wafer visual inspection apparatus, a wafer inspection apparatus, etc.

In addition, the variable direction-of-view observation apparatus 202 of this mode is made in consideration of both the visual observation by observer's direct viewing and a monitor image using an imaging device. However, the invention is not limited to this third mode. For example, in the case of a configuration in which only the monitor image is observed, observation can also be realized by removing an image of the front-and-back observation mirror that has entered from a picked-up observation image, or by generating an image without fetching an image signal equivalent to a front-and-back observation mirror from an imaging device.

Although the description of the above second modified example has been made in conjunction with an example of the case in which the variable direction-of-view observation apparatus of each mode is loaded into an inspection apparatus, such as a microscope, that is, the apparatus is included in the peripheral edge inspection section of the visual inspection apparatus of the invention, the variable direction-of-view observation apparatus of each of the above modes can also be preferably used as a single unit as an observation apparatus in which the direction of view to a test body is variable.

The background art in this case will now be described.

For example, JP-A-9-269298 (Patent Document A), and JP-A-2003-344307 (Patent Document B) discloses an end defect inspection apparatus that exclusively inspects the end face of a wafer in order to detect chips, cracks, etc. generated in the end face.

The following problems exist in the background art.

In the aforementioned wafer edge inspection, generally, in order to detect chips, cracks, etc. of the end face of a wafer, detection is made by visual observation of an image that is obtained by imaging a wafer edge over its whole outer periphery, or by the change of a detection value that is obtained by photoelectric conversion.

Since the end defect inspection apparatus according to Patent Document A is configured so as to detect chips, cracks, etc. from part of diffraction light from the end face of a wafer, it is not possible to observe the front surface or rear surface that leads to the end face of the wafer. Similarly, even in the defect inspection apparatus disclosed in Patent Document 2, it is not possible to detect chips, cracks, etc. of a front or rear surface that leads to the end face of a wafer. Further, in both Patent Documents A and B, it is not possible to perform observation of an edge cut line after the resist of an edge part on the front side is removed. Further, the same applies to a glass substrate used for a liquid crystal display. In this case, it is necessary to perform optimal processing while checking damage, such as chips or cracks generated in an end of the glass substrate, an unnecessary film, etc.

Thus, a variable direction-of-view observation apparatus that can observe a peripheral end face of a test body (end face, and front and rear surfaces of an outer peripheral edge following the end face) from a desired angle has been required.

Such a variable direction-of-view observation apparatus is provided by the following configurations.

(1) A variable direction-of-view observation apparatus including an observation optical system that observes a peripheral end face of a flat plate-like test body, and a mirror part that deflects an optical axis in the observation optical system, to make the optical axis reach the peripheral end face of the test body. Here, while the direction of view is changed by the rotation of the mirror part, the distance between the observation optical system and the peripheral end face of the test body remains substantially constant, and the peripheral end face of the test body is observed.

(2) A visual inspection apparatus including: a base part that is fixed in a position where the peripheral end face of a flat plate-like test body can be observed; an observation optical system that has an optical axis orthogonal to the surface of the test body; a biaxial stage that supports the observation optical system, and is movable in directions orthogonal and parallel to the surface of the test body; a mirror part that is rotatably supported by the biaxial stage to deflect the optical axis in the observation optical system, to make the optical axis reach the peripheral end face of the test body; and a rotation guide part that is provided in the base part, abuts and biases the mirror part so as to allow sliding of the mirror part, and rotates the mirror part so that the optical axis in the observation optical system may be deflected and may be made to reach the peripheral end face of the test body at the time of movement of the orthogonal direction in the biaxial stage. Here, while a direction of view is changed by the rotation of the mirror part, the distance between the observation optical system and the peripheral end face of the test body remains substantially constant, and the peripheral end face of the test body is observed.

(3) The visual inspection apparatus according to the above (2), in which the base part of the variable direction-of-view observation apparatus holds the test body, and is disposed in the vicinity of a stage of a microscope apparatus that is movable and rotatable in triaxial directions orthogonal to one another.

(4) The visual inspection apparatus according to the above (2), in which the rotation guide part of the variable direction-of-view observation apparatus includes a first cam that is provided in the base part, and has a cam surface that is curved so that the mirror part may have a substantially fixed spacing from the peripheral end face of the test body during the movement in the orthogonal direction of the biaxial stage; and a first cam roller that slides along curving of the cam surface at the time of movement of the orthogonal direction of the biaxial stage, and that rotates the mirror part so that the optical axis of the observation optical system may reach the peripheral end face of the test body.

(5) The visual inspection apparatus according to the above (2), in which the variable direction-of-view observation apparatus further includes a stage guide part made up of a second cam that is provided in the base part, and has a cam surface that is curved so that the optical axis in the observation optical system may be maintained in a direction orthogonal to a surface of the test body in the rotation guide part with the movement in the parallel direction at the time of movement of the orthogonal direction of the biaxial stage; and a second cam roller that is provided in the biaxial stage and slides along curving of the cam surface at the time of movement of the orthogonal direction.

(6) The visual inspection apparatus according to the above (2), in which the variable direction-of-view observation apparatus is further provided with two fixed mirrors that are fixed to the base so as to be arranged above and below the front and back surfaces of the test body, and bends the optical axis of the observation optical system in the direction of the peripheral end face of the test body.

(7) The visual inspection apparatus according to the above (2), in which the variable direction-of-view observation apparatus is further provided with two rotary mirrors that are fixed to the base so as to be arranged above and below the surface of the test body, bends the optical axis of the observation optical system in the direction of the peripheral end face of the test body, and are set at a predetermined angle during observation from above or below.

(8) The visual inspection apparatus according to the above (2), in which the variable direction-of-view observation apparatus is further provided with two rotary mirrors that are rotatably arranged in the base so as to be arranged above and below the test body. Here, when the upper surface or lower surface of the test body is observed, any one of the rotary mirrors is rotated, and an observed image of the test body enter the observation optical system via the mirror part, and when the peripheral end face of the test body is observed, the mirror surface of the rotary mirror is set to have an angle of depression with respect to the rotary mirror, and is removed from the field of view of observation in the observation optical system.

(9) A visual inspection apparatus is an observation apparatus loaded into a microscope apparatus that observes the surface of a flat plate-like test body. The observation apparatus includes: a biaxial stage that is movable in a Z direction orthogonal to the surface of the test body, and in an X direction parallel thereto; a base having a driving unit that moves the biaxial stage in the Z direction; a parallel movable plate of a stage made up of a first cam fixed to the base, a roller that is attached to an X-direction movable plate of the biaxial stage, and moves along the first cam, and a tension spring that acts in a direction in which the base and the X-direction movable plate are brought close to each other, an observation optical system of the microscope apparatus whose optical axis is orthogonal to the surface of the test body on the biaxial stage; a mirror part that is arranged between an objective lens within the observation optical system and the focusing position of the objective lens, and is able to arbitrarily deflect the optical axis; a second cam fixed to the base; a second roller that is attached to a rotary arm protruding from a rotary shaft of the mirror part, and moves along the second cam; and a tension spring that is hooked between the rotary arm and the biaxial stage, and acts in a direction in which the second roller is pushed against the second cam. Here wherein, even if the position of the observation optical system and the angle of the rotary mirror are changed according to the first and second cams with the movement of the biaxial stage in the Z direction, thereby arbitrarily changing the direction of view, the distance between the objective lens and the peripheral end face of the test body remains constant while the direction of view is changed with respect to the peripheral end face of the test body and the front and back surfaces following the peripheral end face.

In the variable direction-of-view observation apparatuses described in above (1) to (9), even if the position of the observation optical system and the angle of the rotary mirror are changed by the rotary guide part, thereby changing a direction of view, observation can be made while focusing is always made on the peripheral end face of a test body, and the principal planes (upper and lower surfaces) following the peripheral end face. Therefore, it is possible to provide a variable direction-of-view observation apparatus that can observe a peripheral end face of a test body (end face, and front and rear surfaces of an outer peripheral edge following the end face) from a desired angle.

What is claimed is:

1. A visual inspection apparatus comprising:

a visual inspection section for performing visual inspection of a surface of a workpiece, and a peripheral edge inspection section that acquires an enlarged image of a peripheral edge of the workpiece, wherein the workpiece is a flat plate-like test body, and wherein the peripheral edge inspection section is a variable direction-of-view observation apparatus including:

a base part that is fixed in a position where a peripheral end face of the flat plate-like test body can be observed;

an observation optical system that has an optical axis orthogonal to the surface of the test body;

a biaxial stage that supports the observation optical system, and that is movable in directions orthogonal and parallel to the surface of the test body;

a mirror part that is rotatably supported by the biaxial stage to deflect the optical axis in the observation optical system, to make the optical axis reach the peripheral end face of the test body; and a rotation guide part that is provided in the base part, that abuts and biases the mirror part so as to allow sliding of the mirror part, and that rotates the mirror part so that the optical axis in the observation optical system may be deflected and may be made to reach the peripheral end face of the test body at a time of movement of the biaxial stage in the orthogonal direction, wherein, while a direction of view is changed by the rotation of the mirror part, a distance between the observation optical system and the peripheral end face of the test body is kept substantially constant, and the peripheral end face of the test body is observed.

2. The visual inspection apparatus according to claim 1, wherein the base part of the variable direction-of-view observation apparatus is adapted to hold the test body, and is disposed in a vicinity of a stage of a microscope apparatus that is movable and rotatable in triaxial directions orthogonal to one another.

3. The visual inspection apparatus according to claim 1, wherein the rotation guide part of the variable direction-of-view observation apparatus comprises:

a first cam that is provided in the base part, and has a cam surface that is curved so that the mirror part may have a substantially fixed spacing from the peripheral end face of the test body during the movement of the biaxial stage in the orthogonal direction; and a first cam roller that slides along the curve of the cam surface during the movement of the biaxial stage in the orthogonal direction, and that rotates the mirror part so that the optical axis of the observation optical system may reach the peripheral end face of the test body.

4. The visual inspection apparatus according to claim 1, wherein the variable direction-of-view observation apparatus further includes a stage guide part comprising:

a second cam that is provided in the base part, and has a cam surface that is curved so that the optical axis in the observation optical system may be maintained in a direction orthogonal to the surface of the test body with a parallel movement in the rotation guide part during the movement of the biaxial stage in the orthogonal direction; and a second cam roller that is provided in the biaxial stage and that slides along the curve of the cam surface at the time of the movement in the orthogonal direction.

5. The visual inspection apparatus according to claim 1, wherein the variable direction-of-view observation apparatus further comprises two fixed mirrors that: (i) are fixed to the base part so as to be arranged above and below facing front and back surfaces of the test body, and (ii) bend the optical axis of the observation optical system in the direction of the peripheral end face of the test body.

6. The visual inspection apparatus according to claim 1, wherein the variable direction-of-view observation apparatus further comprises two rotary mirrors that: (i) are fixed to the base part so as to be arranged above and below the surface of the test body, (ii) bend the optical axis of the observation optical system in the direction of the peripheral end face of the test body, and (iii) are set at a predetermined angle during observation from above or below.

7. The visual inspection apparatus according to claim 1, wherein the variable direction-of-view observation apparatus further comprises two rotary mirrors that are rotatably arranged in the base part so as to be arranged above and below the test body, wherein, when an upper surface or a lower surface of the test body is observed, one of the rotary mirrors is rotated, and an observed image of the test body enters the observation optical system via the mirror part, and when the peripheral end face of the test body is observed, a mirror surface of each of the rotary mirrors is set to have an angle of depression with respect to the mirror part, and is removed from a field of view of observation in the observation optical system.

8. A visual inspection apparatus comprising:

a visual inspection section for performing visual inspection of a surface of a workpiece; and a peripheral edge inspection section that acquires an enlarged image of a peripheral edge of the workpiece;

wherein the workpiece is a flat plate-like test body, and the peripheral edge inspection section is an observation apparatus loaded into a microscope apparatus that observes the surface of the flat plate-like test body, wherein the observation apparatus comprises:
- a biaxial stage that is movable in a Z direction orthogonal to the surface of the test body, and in an X direction parallel thereto;
- a base comprising a driving unit that moves the biaxial stage in the Z direction;
- a parallel movable plate of a stage comprising: (i) a first cam fixed to the base, (ii) a roller that is attached to an X-direction movable plate of the biaxial stage, and that moves along the first cam, and (iii) a tension spring that acts in a direction in which the base and the X-direction movable plate are brought close to each other;
- an observation optical system that is of the microscope apparatus and that is on the biaxial stage, and whose optical axis is orthogonal to the surface of the test body;
- a mirror part that is arranged between an objective lens within the observation optical system and a focusing position of the objective lens, and that is able to arbitrarily deflect the optical axis;
- a second cam fixed to the base;
- a second roller that is attached to a rotary arm protruding from a rotary shaft of the mirror part, and that moves along the second cam; and
- a tension spring that is hooked between the rotary arm and the biaxial stage, and that acts in a direction in which the second roller is pushed against the second cam, wherein, even if a position of the observation optical system and an angle of the mirror part are changed according to the first and second cams with the movement of the biaxial stage in the Z direction, thereby arbitrarily changing a direction of view, a distance between the objective lens and the peripheral end face of the test body is kept constant while the direction of view is changed with respect to the peripheral end face of the test body and the front and back surfaces following the peripheral end face.

* * * * *